(12) United States Patent
Kitani

(10) Patent No.: US 7,685,647 B2
(45) Date of Patent: Mar. 23, 2010

(54) INFORMATION PROCESSING APPARATUS

(75) Inventor: Satoshi Kitani, Tokyo (JP)

(73) Assignee: Sony Corporation, Tokyo (JP)

( * ) Notice: Subject to any disclaimer, the term of this patent is extended or adjusted under 35 U.S.C. 154(b) by 474 days.

(21) Appl. No.: 10/596,887

(22) PCT Filed: Jan. 6, 2005

(86) PCT No.: PCT/JP2005/000061

§ 371 (c)(1),
(2), (4) Date: Jun. 28, 2006

(87) PCT Pub. No.: WO2005/067198

PCT Pub. Date: Jul. 21, 2005

(65) Prior Publication Data

US 2007/0143592 A1 Jun. 21, 2007

(30) Foreign Application Priority Data

Jan. 9, 2004 (JP) ............................ P2004-004798
Apr. 19, 2004 (JP) ............................ P2004-122524

(51) Int. Cl.
H04N 7/16 (2006.01)
H04L 29/06 (2006.01)
H04L 9/00 (2006.01)
G06F 12/14 (2006.01)
G06F 21/00 (2006.01)

(52) U.S. Cl. ............................ 726/31; 726/30; 713/164; 713/166; 713/185; 713/189; 713/193; 380/46

(58) Field of Classification Search ........................ None
See application file for complete search history.

(56) References Cited

U.S. PATENT DOCUMENTS

| 5,345,508 | A | * | 9/1994 | Lynn et al. ..................... 380/46 |
| 5,883,958 | A | | 3/1999 | Ishiguro et al. |
| 6,460,137 | B1 | | 10/2002 | Akiyama et al. |
| 7,275,161 | B2 | * | 9/2007 | Ochi et al. ................... 713/182 |

FOREIGN PATENT DOCUMENTS

| EP | 1 037 209 | 9/2000 |
| JP | 08-335040 | 12/1996 |
| JP | 10-65662 | 3/1998 |

(Continued)

OTHER PUBLICATIONS

WO 2003/038571 A1 May 2003 WIPO Ochi, Makoto et al.*

*Primary Examiner*—Kaveh Abrishamkar
(74) *Attorney, Agent, or Firm*—K&L Gates LLP

(57) ABSTRACT

The present invention relates to an information processing apparatus, an information processing method, a program, and a recording medium for sending and receiving data in a manner enhancing security. A host and a drive unit are interconnected by a suitable bus and exchange data over that bus. The host requests the drive unit periodically to issue an initializing vector IV for use in encrypting and decrypting the data exchanged over the bus. The drive unit supplies the initializing vector IV to the host on request. If these steps are not carried out periodically, the drive unit stops outputting data to the host. The present invention is adapted advantageously to personal computers equipped with a drive unit for reproducing data from a recording medium.

4 Claims, 27 Drawing Sheets

FOREIGN PATENT DOCUMENTS

| | | |
|---|---|---|
| JP | 2000-330872 | 11/2000 |
| JP | 2001-306401 | 11/2001 |
| JP | 2001-521697 | 11/2001 |
| JP | 2005-505873 | 2/2005 |
| WO | 98/48540 | 10/1998 |
| WO | 01/52474 | 7/2001 |
| WO | 03/034425 | 4/2003 |

* cited by examiner

| Bit<br>Byte | 7 | 6 | 5 | 4 | 3 | 2 | 1 | 0 |
|---|---|---|---|---|---|---|---|---|
| 0 | Operation Code | | | | | | | |
| 1 | LUN(Obsolete) | | | DPO(0) | FUA | Reserved | Reserved | RelAdr |
| 2 | (MSB) | | | | | | | |
| 3 | Logical Block Address | | | | | | | |
| 4 | | | | | | | | |
| 5 | | | | | | | | (LSB) |
| 6 | (MSB) | | | | | | | |
| 7 | Transfer Length | | | | | | | |
| 8 | | | | | | | | |
| 9 | | | | | | | | (LSB) |
| 10 | Streaming | Reserved | | | | | | |
| 11 | Vendor-Specific | | | | | NACA | Flag | Link |

INFORMATION PROCESSING APPARATUS

CROSS REFERENCE TO RELATED APPLICATIONS

The present application claims priority to Japanese Patent Document Nos. P2004-004798 filed on Jan. 9, 2004 and P2004-122524 filed on Apr. 19, 2004, the disclosures of which are herein incorporated by reference.

BACKGROUND

The present invention relates to an information processing apparatus, an information processing method, a program, and a recording medium. More particularly, the invention relates to an information processing apparatus, an information processing method, a program, and a recording medium for carrying out processes associated with encryption.

It is becoming commonplace for diverse kinds of apparatuses to exchange digital data therebetween. Given the trend, it has become necessary to take measures against illicit uses of digital data which, by nature, does not corrupt in quality (i.e., picture and sound quality) when used or copied legitimately or otherwise (e.g., refer to Patent Document 1).

With DVD (digital versatile discs) and similar recording media gaining widespread acceptance today, it is easy to record a very large amount of data like a movie onto one piece of such media (e.g., disc) as digital information. Where movie information or similar data can be recorded as digital information, it is becoming all the more important to prevent illegal copying to protect copyright holder's interests.

DVD videos (i.e., video content-packed DVD) adopt CSS (Content Scramble System) as copyright protection technology. FIG. 1 is a block diagram showing a structure of a recording medium on which data encrypted by the CSS technology is recorded, along with a structure of an apparatus for reproducing data from that medium.

FIG. 1 indicates a disc 11 as a typical recording medium. The disc 11 retains a secured disc key 21 for identifying the disc 11, an encrypted title key 22 embedded in data at predetermined intervals, and scrambled data 23. Illustratively, if a movie is recorded on the disc 11, the title key 22 is provided illustratively for each chapter.

The disc key 21 and title key 22 are recorded in encrypted format (or in a manner resistant to abusive retrieval) on the disc 11. The data 23 is scrambled through the use of the title key 22 when recorded on the disc 11.

A player 12 reproduces the data 23 by reading keys and data from the disc 11. The player 23 has decryption devices 32 and 33, a descrambling device 34, and a decoder 35. The player 12 also has a management device (not shown) that manages a master key 31.

The decryption device 32 decrypts the disc key 21 read from the disc 11 by use of the master key 31, and supplies the decrypted disc key 21 to the decryption device 33. The title key 22 retrieved from the disc 11 is also supplied to the decryption device 33. Using the decrypted disc key 21, the decryption device 33 decrypts the encrypted title key 22. The decrypted title key 22 is fed to the descrambling device 34. The data 23 retrieved from the disc 11 is also fed to the descrambling device 34.

The data 23 to be read from the disc 11 and supplied to the player 12 has been compressed by a predetermined compression standard (e.g., MPEG (Moving Picture Experts Group) standard) before being scrambled by use of the title key 22. The descrambling device 34 descrambles the data 23 using the title key 22.

The descrambled data 23 is supplied to the decoder 35. The decoder 35 decodes the data 23 from the descrambling device 34 in accordance with a predetermined decoding standard (e.g., MPEG standard). The decoded data 36 is supplied to a display unit or like equipment, not shown.

The player 12 shown in FIG. 1 is illustratively a device dedicated to the reproduction of data from the disc 11 such as DVD. Alternatively, the dedicated player 12 may be replaced by a personal computer capable of reproducing data from the disc 11.

FIG. 2 shows a structure of a setup in which the disc 11 such as DVD is played illustratively by a personal computer or similar equipment. In this setup, a drive unit 51 reads data from the disc 11, and a host 52 processes the data read out by the drive unit 51. The drive unit 51 and host 52 shown in FIG. 2 include functions that may be implemented by application software.

As in the setup of FIG. 1, the disc 11 retains the disc key 21, title key 22, and data 23. The drive unit 51 is structured to include an authentication processing device 62 and bus encryption devices 62 and 63.

The host 52 has an authentication processing device 71, bus decryption devices 72 and 73, decryption devices 74 and 75, a descrambling device 76, and a decoder 77. The host 52 also has a management device (not shown) that manages the master key 31.

The authentication processing device 51 of the drive unit 51 and the authentication processing device 71 of the host 52 authenticate one another. Only when the process of mutual authentication is normally completed, can data be sent and received between the drive unit 51 and the host 52. Following the successful authentication process, the authentication processing devices 61 and 71 issue a key called a session key each (for shared use).

After the normal authentication process, the disc key 21 read from the disc 11 is encrypted by the bus encryption device 62 of the drive unit 51. The bus encryption device 62 is also supplied with the session key issued by the authentication processing device 61. Using the session key, the bus encryption device 62 encrypts the retrieved disc key 21 and outputs the encrypted disc key 21 to the host 71.

Likewise, the bus encryption device 63 encrypts the title key 22 read from the disc 11 by use of the session key issued by the authentication processing device 61, and outputs the encrypted title key 22 to the host 52. The data 23 retrieved from the disc 11 is supplied from the drive unit 51 directly to the host 52.

The bus decryption device 72 of the host 52 decrypts the encrypted disc key 21 sent from the bus encryption device 62 of the drive unit 51 through the use of the session key issued by the authentication processing device 71. The decrypted disc key 21 is fed to the decryption unit 74. The decryption unit 74 is also fed with the master key 31. Using the master key 31, the decryption device 74 decrypts the disc key 21 supplied from the bus decryption device 72 and sends the decrypted disc key 21 to the decryption device 75.

The decryption device 75 is also supplied with the title key 22 from the bus decryption device 73. The title key 22 has been decrypted by the bus decryption device 73 using the session key issued by the authentication processing device 71.

The decryption device 75 decrypts the encrypted title key 22 using the decrypted disc key 21. The decrypted title key 22 is supplied to the descrambling device 76. The descrambling device 76 is also supplied with the data 23 read from the disc 11.

The data 23 retrieved from the disc 11 has been compressed by a predetermined compression algorithm and scrambled by use of the title key 22. The descrambling device 76 first descrambles the data 23 using the supplied title key 22.

The descrambled data 23 is supplied to the decoder 77. The decoder 77 decodes the supplied data 23 by a predetermined decoding standard (e.g., MPEG standard). The decoded data 36 is supplied to a display unit or like equipment, not shown.

As described, the drive unit 51 loaded with the disc 11 and the host 52 for processing data held on the disc 11 authenticate one another before proceeding to reproduce the data 23 retrieved from the disc 11. Following a successful process of authentication, encrypted keys and data are sent and received between the drive unit 51 and the host 52.

It should be noted that data is actually sent and received between the drive unit 51 and the host 52 only after the authentication process. That is because the drive unit 51 and the host 52, connected by an appropriate bus (not shown), are designed to prevent the data from getting tapped illicitly from that bus.

Given below with reference to the flowchart of FIG. 3 is an additional description of the authentication process carried out between the authentication processing devices 61 and 71. In step S11, a check is made to determine whether the disc 11 is loaded (i.e., set) into the drive unit 51. A standby state is maintained until the disc 11 is found loaded into the drive unit 51 in step S11 (i.e., the process of step S11 is repeated).

If in step S11 the disc 11 is found loaded into the drive unit 51, step S12 is reached. In step S12, the authentication processing devices 61 and 71 authenticate one another. Unless and until the process of mutual authentication is normally completed, the subsequent steps will not be carried out.

Following the successful mutual authentication process, the authentication processing devices 61 and 71 generate a session key each. In step S13, a check is made to determine whether the process of mutual authentication has normally ended and the session key generation is successfully completed. The process of step S12 is repeated until it is found complete in step S13. Thereafter, control is passed on to step S14.

In step S14, a state is established in which scrambled data is authorized to be sent and received (i.e., output from the drive unit 51). In this case, the scrambled data is the data 23 (FIG. 2) that is authorized to be output from the drive unit 51 to the host 52.

More description will be made of the "authorized" state below. Under instructions from the host 52, the drive unit 51 reads the data 23 in the authorize state. With such authorization yet to be made, the drive unit 51 does not output the data 23, and instead returns an error message upon receipt of an instruction from the host 52 to read (output) the data 23.

With the authorized state in effect and given the instruction from the host 52, the drive unit 51 retrieves the data 23 from the disc 11. The retrieved data 23 is output to the host 52.

Once the authorized state is established, reproduction of the scrambled data 23 is repeated unless an interrupt condition such as unloading of the disc 11 from the drive unit 51 takes place.

With the scrambled data 23 authorized to be output, step S15 is reached. In step S15, a check is made continuously to determine whether the disc 11 is unloaded from the drive unit 51. When the disc 11 is found unloaded from the drive unit 51, control is returned to step S11 and the subsequent steps are repeated.

Data reproduction is also terminated when the drive is reset or switched off. Step S11 is then reached again as needed and the subsequent steps are repeated.

As described, following the normal termination of mutual authentication between the drive unit 51 and the host 52, the drive unit 51 keeps reading the data 23 from the loaded disc 11 and outputting the retrieved data 23 to the host 52 until the disc 11 is unloaded. The process is continued unless and until another instruction is given by the host 52.

A brief comment will be made here on some known techniques of encryption performed by encryption equipment such as the bus encryption device 62. Varieties of encryption algorithms have been proposed. One such encryption (and decryption) algorithm called CBC (Cipher Block Chaining) is explained below.

The CBC encryption algorithm is a technique that involves exclusively ORing each block of data in unencrypted form with the preceding block in encrypted form so as to generate each encrypted block of data. FIG. 4 shows a typical circuit for encryption by the CBC algorithm.

The target data to be encrypted is turned into blocks in predetermined increments (e.g., 16 bytes if AES (Advanced Encryption Standard) is used as the block encryption scheme). A first block is supplied to an XOR circuit 101-1, a second block following the first block is fed to another XOR circuit 101-2, a third block following the second block is sent to another XOR circuit 101-3, and so on. There are provided as many XOR circuits as a predetermined number of stages (N stages in this example) so that blocks of data in unencrypted form may be input successively to the XOR circuits 101-1 to 101-N.

The first block output from the XOR circuit 101-1 is supplied to an encryption device 102-1. The encryption device 102-1 encrypts the supplied first block using a key Ek. Thus, the first block is encrypted.

The encrypted first block output from the encryption device 102-1 is also sent to the XOR circuit 101-2 for the exclusive OR operation with the second block. The result of the XOR operation is fed to another encryption device 102-2 that encrypts the supplied data using the same key Ek.

According to the CBC encryption, as outlined above, each block of data in unencrypted form is XORed with the preceding block in encrypted form. The resulting block of data is encrypted by use of a predetermined encryption key. The block of data thus encrypted is XORed with the next block of data. Thus each current block is chained to the preceding block successively to generate data in encrypted form.

Whereas the second and subsequent blocks of data are each XORed with the preceding block, the first block cannot be XORed with its preceding block which obviously does not exist. Thus an initializing vector (IV) is introduced and XORed with the first block.

Described below with reference to FIG. 5 is a decryption circuit (e.g., bus decryption device 72 (FIG. 2)) based on the CBC algorithm.

Encrypted data is turned into blocks in predetermined increments (e.g., 16 bytes if AES (Advanced Encryption Standard) is used as the block encryption scheme), as discussed above. A first block of data is supplied to a decryption device 122-1, a second block following the first block is fed to another decryption device 122-2, a third block following the second block is sent to another decryption device 122-3, and so on. There are provided as many decryption devices as a predetermined number of stages (N stages in this example) so that blocks of data in encrypted form may be input successively to the decryption devices 122-1 to 122-N.

The decryption devices 122-1 to 122-N decrypt the respectively input data using a key Dk each. The data output from the decryption devices 122-1 to 122-N are supplied to XOR circuits 121-1 to 121-N respectively. The XOR circuits 121-2 to 121-N are also supplied with the data fed to the respectively preceding decryption blocks 122-1 to 122-N-1.

As described, the decryption based on the CBC algorithm is accomplished when each target block of data in decrypted form is XORed with the preceding block in encrypted form.

While the second and subsequent blocks of data are each XORed with the preceding block, the first block cannot be XORed with its preceding block which obviously does not exist. Thus an initializing vector (IV) is introduced and XORed with the first block.

The foregoing description has given an outline of how encryption and decryption are typically executed.

[Patent Document 1]

Japanese Patent No. 3252706

Where the data 23 is to be reproduced from the disc 11 by the drive unit 51 in conjunction with the host 52 as shown in FIG. 2, the data 23 is authorized to be output from the drive unit 51 following the successful process of mutual authentication between the drive unit 51 and the host 52. The process was explained above in reference to the flowchart of FIG. 3.

Suppose that the host 52 starts up an application A and that the application A thus activated prompts the authentication processing device 71 to carry out the authentication process. In this case, normal execution of the authentication process by the application A with regard to the drive unit 51 brings about a state in which the data 23 is authorized to be read from the disc 11 and output by the drive unit 51.

In that state, the data 23 is authorized to be output continuously by the drive unit 51 unless and until the disc 11 is unloaded from the drive unit 51. Suppose now that with the authorized state in effect, an application B is started up by the host 52 and that the application B, instead of the application A, starts giving instructions including one for reading out the data 23.

In that case, the drive unit 51 and the application B do not authenticate one another. However, because the drive unit 51 is held in the state in which the data 23 is authorized to be output, the data 23 is left being output from the drive unit 51 to the host 52 (i.e., application B). As a result, the data 23 can be recorded by the application B to a hard disc drive (HDD) 141 as part of the host 52.

Although recording of the data 23 onto the HDD 141 is illegal, the drive unit 51 proceeds to output the data 23 under instructions from the application B. This kind of abuse has been left unchecked with existing setups.

The data 23 stored on the HDD 141 is scrambled and cannot be reproduced as is. Still, because there are applications for descrambling data, it is virtually impossible to prevent illicit uses of the data 23 once it is recorded to the HDD 141.

As described, once the authentication process is normally accomplished and the data 23 is authorized to be output from the drive unit 51, the data 23 becomes vulnerable to theft.

Other abuses of data are explained below with reference to FIG. 7. The drive unit 51 and the host 52 are interconnected by a suitable bus and exchange the data 23 therebetween over that bus. As in the case discussed above with reference to FIG. 6, the application A on the host side performs mutual authentication with the drive unit 51. After the normally completed process of authentication, the data 23 is authorized to be output from the drive 51.

If the host 52 has a monitor 151 for monitoring data that is sent and received over the bus, that monitor 151 can be used to acquire (i.e., monitor) the data 23 from the bus. In other words, the data 23 output from the drive unit 51 can be supplied both to the application A and to the monitor 151.

It is thus possible for the host 52 to store onto the HDD 141 the data 23 acquired by the monitor 151. This is another way in which the data 23 could be abused.

As described, existing setups could let the monitoring function be utilized to steal or otherwise abuse the data exchanged over the bus.

Methods have been proposed to encrypt the data 23 so that the data 23 exchanged over the bus will not be stolen from the bus. One such method is described here with reference to FIG. 8. In the ensuing description, the data output from the drive unit 51 to the host 52 will be referred to as transfer data 171.

The transfer data 171 is handled in data packets of 2,048 bytes (2K bytes) each. Where the drive unit 51 and host 52 are interconnected by a suitable bus as described above, a bus interface 183 for controlling the bus is installed to handle data in predetermined increments. Illustratively, if the bus interface 183 is based on ATAPI (AT Attachment with Packet Interface), it is stipulated that the data increment be 2,048 bytes.

If the transfer data 171 is assumed to occur in data packets of 2,048 bytes, each packet is made up of a 16-byte initializing vector IV and a 2,032-byte data part as indicated in FIG. 8. In this data packet, the 2,032-byte data part is encrypted by an encryption device 181. Although not shown in FIG. 8, the encryption device 181 encrypts each data part using a session key Ks issued by the authorization processing device 181 (see FIG. 2).

The encryption device 181 performs its encryption process illustratively through the use of the CBC algorithm. The CBC-based encryption requires that the encryption device 181 be structured internally as shown in FIG. 4. As explained above in reference to FIG. 4, the encryption device 181 also utilizes the initializing vector IV when carrying out the encryption. That is, given each data packet of the transfer data 171, the encryption device 181 encrypts the 2,038-byte data part using the 16-byte initializing vector IV included in the same data packet as well as the session key Ks issued by the authentication processing device 181.

The data packets encrypted by the encryption device 181 are each a 2,048-byte data packet that can be handled by the bus interface 183. Each data packet with its data part encrypted is supplied to a decryption device 182 of the host 52. The decryption device 182 decrypts the encrypted data using the initializing vector IV included in the supplied data packet and the session key Ks issued by the authentication processing device 71 (FIG. 2).

Although the host 52 receives the encrypted data, that data can be decrypted by the host 52 using the initializing vector IV furnished together with the data in question. In this manner, the host 52 can reproduce the data output from the drive unit 51.

When the data exchanged through the bus interface 183 is encrypted, the data will not be abused as long as it is not decrypted even if the data exchanged through the bus interface 183 is tapped. In this manner, misappropriation of data is supposed to be prevented. However, there are some problems with this scheme as will be outlined in the following description:

Referring again to FIG. 8, the initializing vector IV is part of the transfer data 171. When the initializing vector IV is to be included in the transfer data 171, the vector is written to the disc 11 together with other data. That means the initializing vector IV cannot be varied randomly (i.e., the initializing vector IV written on the disc must be used as is, without change).

It might be possible, with no initializing vector IV written on the disc 11, to have the drive unit 51 generate the initializing vector IV randomly so as to get the vector IV included in the transfer data 171. However, this is where a restricting condition is imposed: when the initializing vector IV is to be included in the transfer data 171, the vector must be provided illustratively with a header and the like in distinction from the data to be encrypted.

Under that condition, the drive unit 51 may be arranged to generate randomly the initializing vector IV but is subject to certain constraints on the randomized vector generation. Ultimately, there is no guarantee that the drive unit 51 can always generate the initializing vector IV on a random basis (i.e., there may occur a fixed pattern during initializing vector generation).

If the initializing vector IV cannot be varied randomly, i.e., if a fixed pattern is expected to appear during initializing vector generation, there may be the following problem:

Illustratively, the format of e-mail has a fixed pattern made up of the recipient's address, the sender's address, a subject, and a message. If the data of that pattern (in plain text) is encrypted, the encrypted data also presents a pattern that may draw the attention of a third party (i.e., attacker). A third party could then proceed to decrypt at least in part the encrypted data.

In another example where music data is prepared for repeated reproduction, the preparatory encryption involves encrypting data in the same plain text repeatedly, which results in encrypted data having a repetitive pattern. As in the preceding example, the encrypted data presents a pattern that is vulnerable to abusive decryption.

Under these circumstances, where there is plain text data with a fixed pattern to be encrypted (e.g., for the same data to be encrypted a plurality of times), the first block of data is supplemented with an initializing vector IV so as to nullify any similar pattern that may appear in the encrypted data. Adding the initializing vector IV to the first block upon encryption prevents the same pattern as that in the plain text data block from taking shape, which makes eventual decryption more difficult. As another benefit, addition of the initializing vector IV at encryption time makes it easy to predict a single key that may be used to encrypt a large amount of data.

It is for these reasons that the initializing vector IV is often added to the first block of data before the subsequent blocks are encrypted.

Updating the initializing vector IV at suitable intervals makes it more difficult to determine whether given plain text data has a particular pattern. This contributes to preventing unscrupulous data substitution or falsification. (Reference: NIST Special Publication 800-38A 2001 Edition, Recommendation for Block Cipher Modes of Operation, Methods and Techniques, APPENDIX C Generation of Counter Blocks)

In other words, if the same initializing vector IV is used repeatedly, the practice cannot offer the benefit of periodically updating the vector IV described above. As a result, to use the same initializing vector IV repeatedly makes it difficult to determine whether given plaintext data has a particular pattern and cannot prevent data substitution or falsification.

Obviously, it is preferable to update the initializing vector IV as described above.

Where arrangements are made to update the initializing vector IV, methods such as one shown in FIG. 9 are worked out whereby data is sent and received. In the example of FIG. 9, the transfer data 191 is constituted by blocks of 2,048-byte data supplemented with a 16-byte initializing vector IV each. The added vector IV makes up a 2064-byte data block that can be sent and received through the bus interface 183.

When the initializing vector IV is added to the transfer data 191 (i.e., where the initializing vector IV is not included beforehand in the transfer data 191), the drive unit 51 can be arranged to generate the vector IV randomly. The randomly generated initializing vector IV is then added to the transfer data 191.

However, addition of the initializing vector IV to data signifies that a special sector size of 2,064 bytes (where IV=16 bytes) is introduced to the PC Drive Interface that handles data typically in increments of 2,048 bytes. What is created here is a nonstandard format that is not compatible with the environment of a personal computer (PC). The incompatible environment includes the commonly used ATAPI Device Driver, and UDF (Universal Data Format) FS Driver that handles sector sizes of 2,048 bytes or 4,096 bytes.

The incompatibility with the PC environment must be circumvented by making special modifications in terms of hardware and/or software. The exercise is costly and laborious. After the modifications, the speed of data processing is bound to be reduced.

SUMMARY

The present invention has been devised in order to solve the aforementioned problem and one of its objects is to enable the state of authorizing data output by the drive unit to be canceled as needed so as to prevent data theft. Another object of the present invention is to provide security-enhancing arrangements allowing the initializing vector IV to be updated even in a setup where a general-purpose bus is used so that data exchanged over that bus will not be stolen.

In carrying out the invention and according to one embodiment of the present invention, there is provided an information processing apparatus including: transfer controlling means for controlling transfer of data; counting means for counting the number of times the transfer controlling means has controlled the transfer of the data; first determining means for determining whether the number of times counted by the counting means is at least equal to a predetermined threshold; first instructing means which, if the number of times is found at least equal to the threshold by the first determining means, then gives the transfer controlling means an instruction to stop the transfer of the data; generating means for generating an initializing vector for use in either encrypting or decrypting the data of which the transfer is controlled by the transfer controlling means; second determining means for determining whether an instruction to have the initializing vector supplied is given by an external apparatus to and from which is sent and received the data of which the transfer is controlled by the transfer controlling means; and second instructing means which, if the instruction to have the initializing vector supplied is found given by the second determining means, then gives the generating means an instruction to generate the initializing vector while giving the counting means an instruction to reset the number of times having been counted.

Preferably, the information processing apparatus of the present invention may further include outputting means which, if the instruction is given by the first instructing means, then outputs to the external apparatus a message saying that the transfer of the data is stopped.

According to another embodiment of the present invention, there is provided an information processing method including the steps of: controlling transfer of data; counting the number of times the transfer controlling step has controlled the transfer of the data; firstly determining whether the number of times counted in the counting step is at least equal to a predetermined threshold; if the number of times is found at least equal to the threshold in the first determining step, then firstly giving in the transfer controlling step an instruction to stop the transfer of the data; generating an initializing vector for use in either encrypting or decrypting the data of which the transfer is controlled in the transfer controlling step; secondly determining whether an instruction to have the initializing vector supplied is given by an external apparatus to and from which is sent and received the data of which the transfer is controlled in the transfer controlling step; and if the instruction to have the initializing vector supplied is found given in the second determining step, then secondly giving in the generating step an instruction to generate the initializing vector while giving in the counting step an instruction to reset the number of times having been counted.

According to a further embodiment of the present invention, there is provided a program for causing a computer to carry out a procedure including the steps of: controlling transfer of data; counting the number of times the transfer controlling step has controlled the transfer of the data; firstly determining whether the number of times counted in the counting step is at least equal to a predetermined threshold; if the number of times is found at least equal to the threshold in the first determining step, then firstly giving in the transfer controlling step an instruction to stop the transfer of the data; generating an initializing vector for use in either encrypting or decrypting the data of which the transfer is controlled in the transfer controlling step; secondly determining whether an instruction to have the initializing vector supplied is given by an external apparatus to and from which is sent and received the data of which the transfer is controlled in the transfer controlling step; and if the instruction to have the initializing vector supplied is found given in the second determining step, then secondly giving in the generating step an instruction to generate the initializing vector while giving in the counting step an instruction to reset the number of times having been counted.

According to an even further embodiment of the present invention, there is provided a recording medium which records a computer-readable program for causing a computer to carry out a procedure including the steps of: controlling transfer of data; counting the number of times the transfer controlling step has controlled the transfer of the data; firstly determining whether the number of times counted in the counting step is at least equal to a predetermined threshold; if the number of times is found at least equal to the threshold in the first determining step, then firstly giving in the transfer controlling step an instruction to stop the transfer of the data; generating an initializing vector for use in either encrypting or decrypting the data of which the transfer is controlled in the transfer controlling step; secondly determining whether an instruction to have the initializing vector supplied is given by an external apparatus to and from which is sent and received the data of which the transfer is controlled in the transfer controlling step; and if the instruction to have the initializing vector supplied is found given in the second determining step, then secondly giving in the generating step an instruction to generate the initializing vector while giving in the counting step an instruction to reset the number of times having been counted.

Where the information processing apparatus, information processing method, and program according to the present invention are in use, the sending and receiving of data will be stopped unless instructions are given periodically to have the initializing vector supplied.

According to the present invention, security is thus enhanced on the bus for sending and receiving data between apparatuses.

According to the present invention, following the process of authentication between an apparatus for reading data from a recording medium on the one hand and another apparatus for handling data received from the data-reading apparatus on the other hand, the data-reading apparatus is authorized to output the retrieved data to the other apparatus but the authorized state is set to be canceled (or updated) as needed. This makes it possible to prevent data leaks due to illicit access after the data-reading apparatus is authorized to output data to another apparatus.

According to the present invention, the initializing vector for use in encryption can be updated randomly. That means encrypting the same data repeatedly will not result in generating the same encrypted sentences. This contributes to preventing data substitution, falsification, or other illicit uses of data.

Furthermore, according to the present invention, updating the initializing vector does not hamper the use of a general-purpose bus interface as well as the UDF FS Driver provided as standard by the OS (Operating System). There is no need to make onerous modifications in the environment between interconnected apparatuses in order to update the initializing vector.

Additional features and advantages of the present invention are described in, and will be apparent from, the following Detailed Description and the Figures.

BRIEF DESCRIPTION OF THE FIGURES.

FIG. 1 is a block diagram showing a structure of a typical reproducing apparatus.

FIG. 2 is a block diagram showing another structure of the typical reproducing apparatus.

FIG. 3 is a flowchart of steps constituting an authentication process.

FIG. 4 is a circuit diagram of a typical circuit for encryption.

FIG. 5 is a circuit diagram of a typical circuit for decryption.

FIG. 6 is a schematic view illustrating a problem with the typical reproducing apparatus.

FIG. 7 is a schematic view illustrating another problem with the typical reproducing apparatus.

FIG. 8 is a schematic view illustrating a problem encountered when an initializing vector IV is sent and received.

FIG. 9 is a schematic view illustrating another problem encountered when the initializing vector IV is sent and received.

FIG. 10 is a block diagram of a system practiced as one embodiment of the present invention.

[FIG. 11]
FIG. 11 is a schematic view explaining drivers involved in sending and receiving data.

FIG. 12 is a flowchart of steps constituting a process performed by a drive unit.

FIG. 13 is a flowchart continued from the flowchart of FIG. 12.

FIG. 14 is a timing chart with regard to the sending and receiving of the initializing vector IV.

FIG. 15 is another timing chart with regard to the sending and receiving of the initializing vector IV.

FIG. 16 is another timing chart with regard to the sending and receiving of the initializing vector IV.

FIG. 17 is a timing chart with regard to the sending and receiving of data.

[FIG. 18]
FIG. 18 is a schematic view showing a structure of a command packet.

FIG. 19 is a block diagram of a system practiced as a variation of the embodiment of this invention.

FIG. 20 is another timing chart with regard to the sending and receiving of data.

FIG. 21 is a block diagram showing a structure of a recording apparatus practiced as a second embodiment of the present invention.

FIG. 22 is another timing chart with regard to the sending and receiving of the initializing vector IV.

FIG. 23 is another timing chart with regard to the sending and receiving of the initializing vector IV.

FIG. 24 is a flowchart of steps constituting a process performed by a host.

FIG. 25 is a flowchart continued from the flowchart of FIG. 24.

FIG. 26 is a flowchart of steps constituting another process performed by the drive unit.

FIG. 27 is a flowchart continued from the flowchart of FIG. 26.

Figure 1:
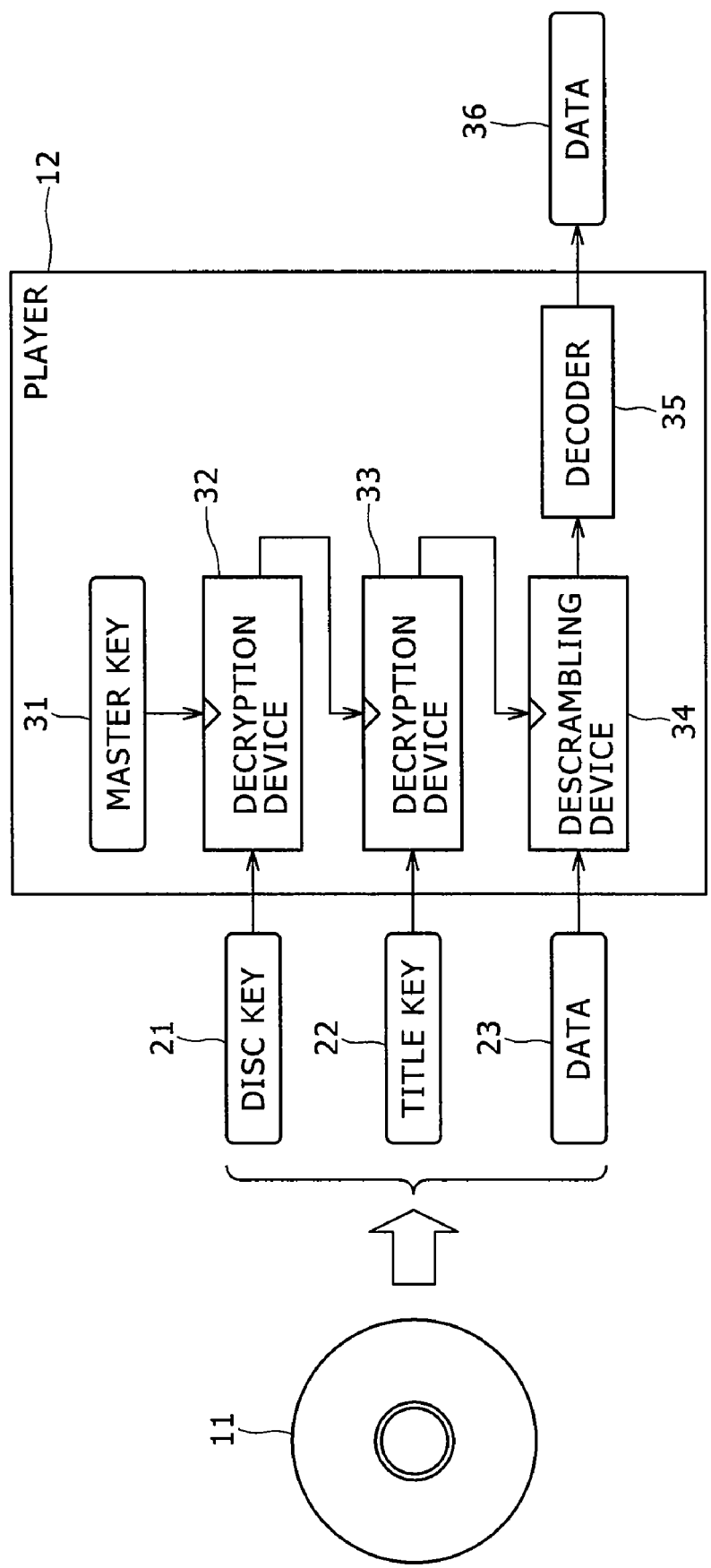
[FIG. 1]
Figure 2:
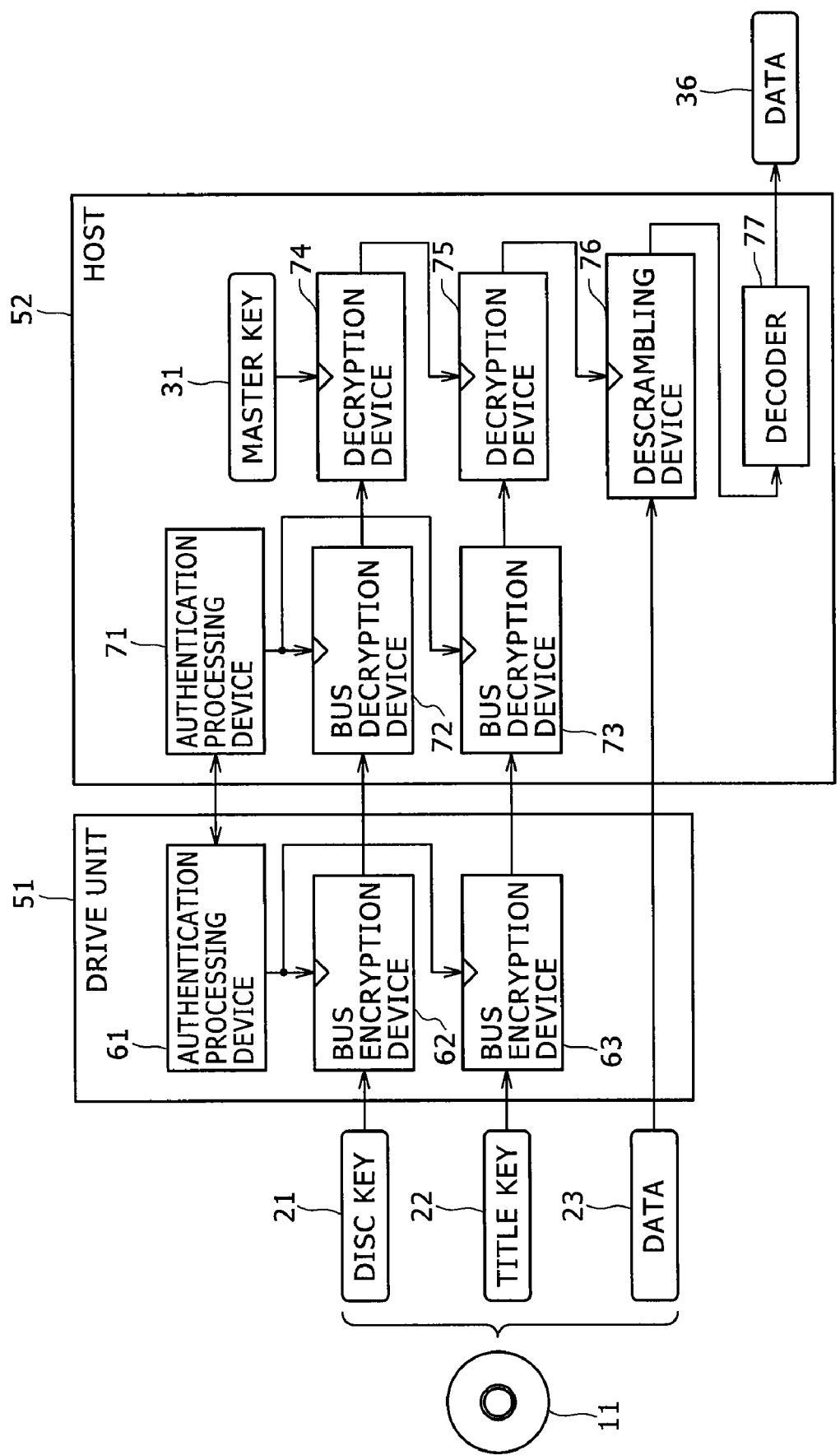
[FIG. 2]
Figure 3:
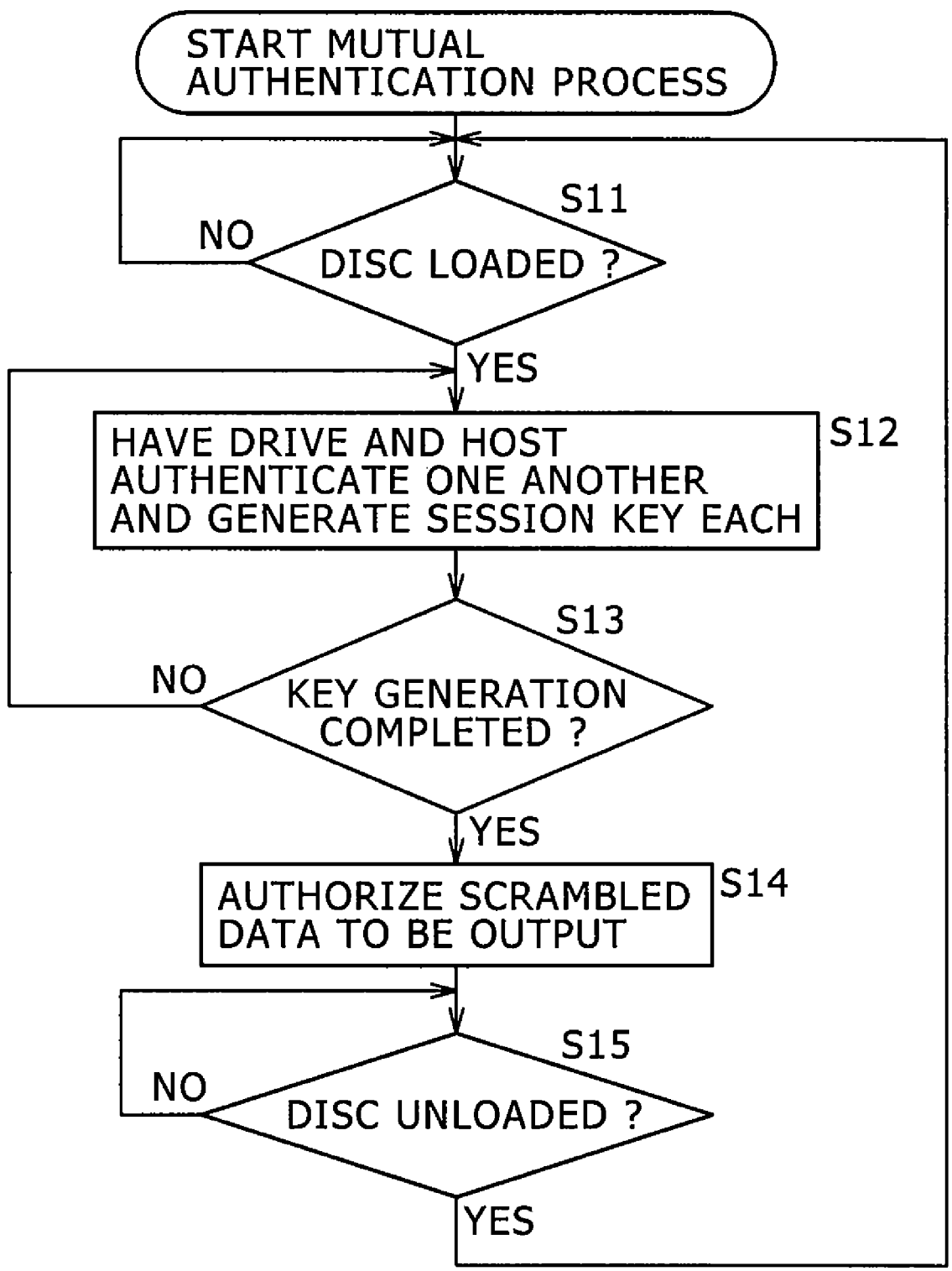
[FIG. 3]
Figure 4:
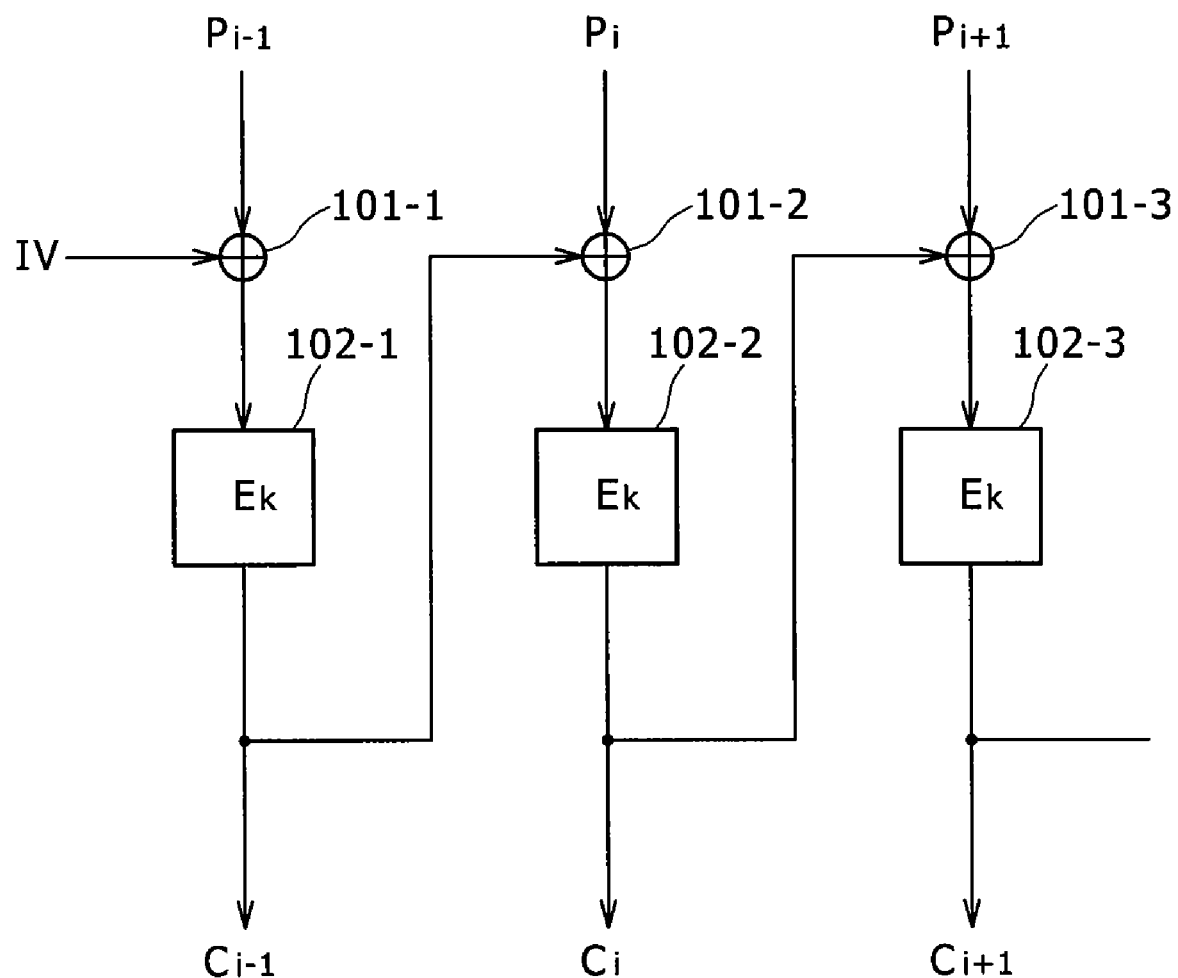
[FIG. 4]
Figure 5:
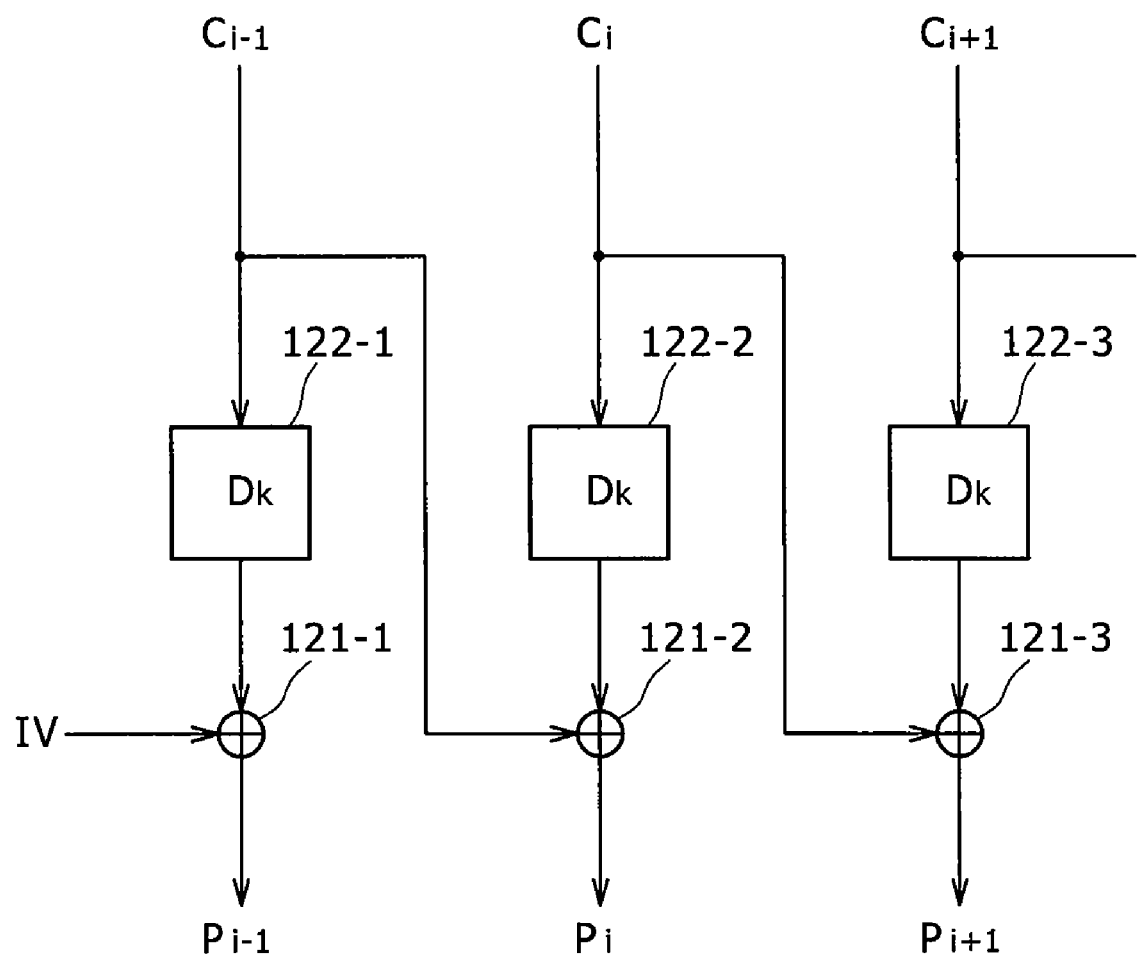
[FIG. 5]
Figure 6:
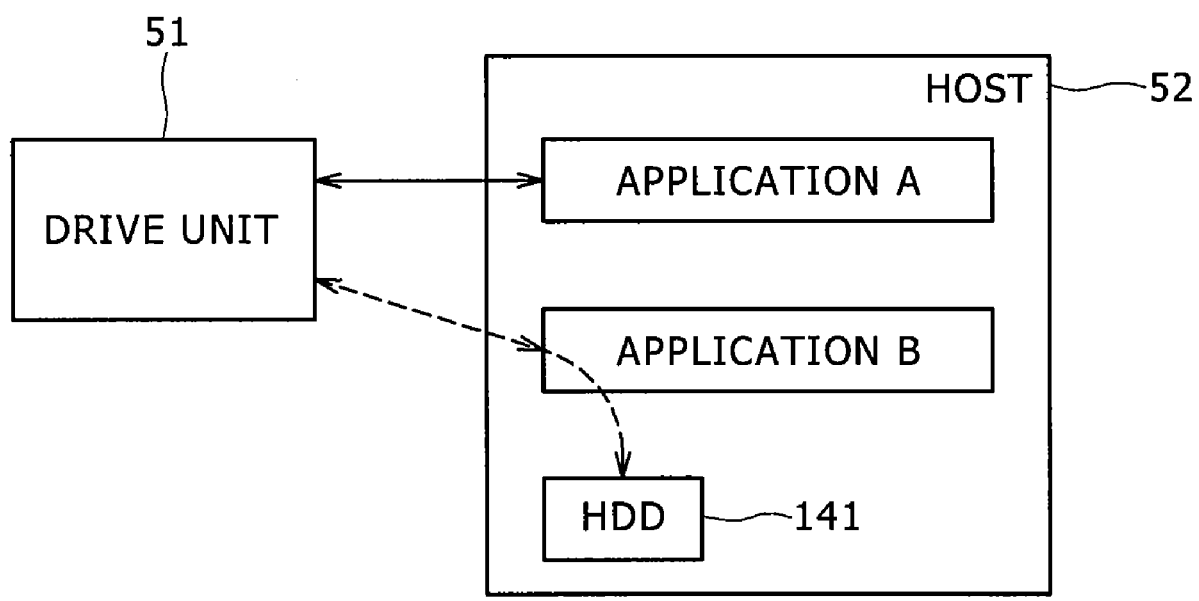
[FIG. 6]
Figure 7:
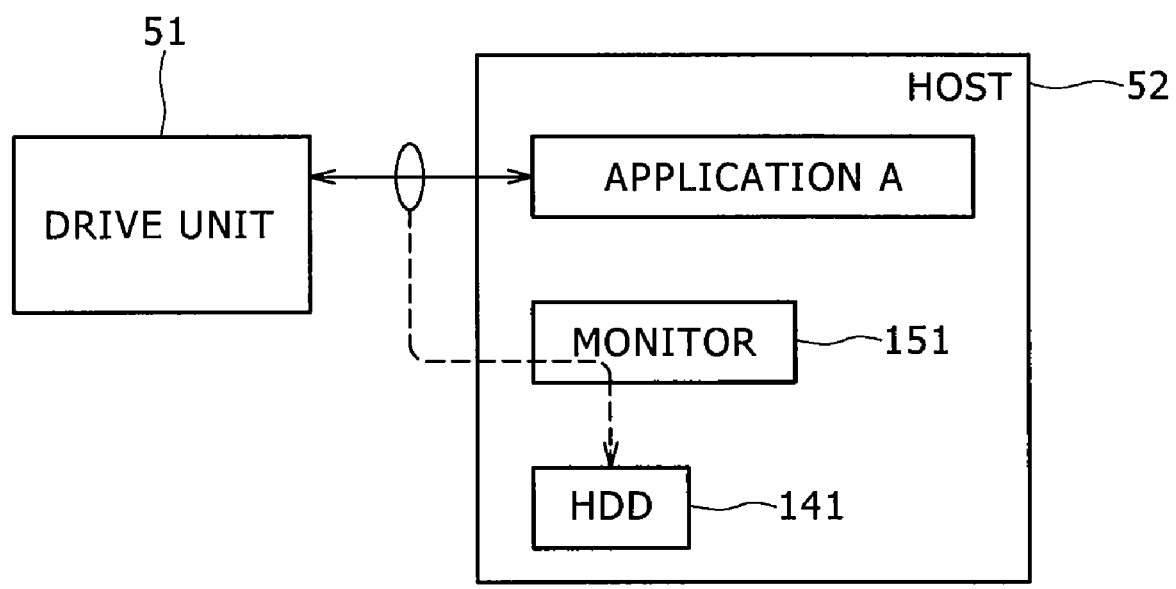
[FIG. 7]
Figure 8:
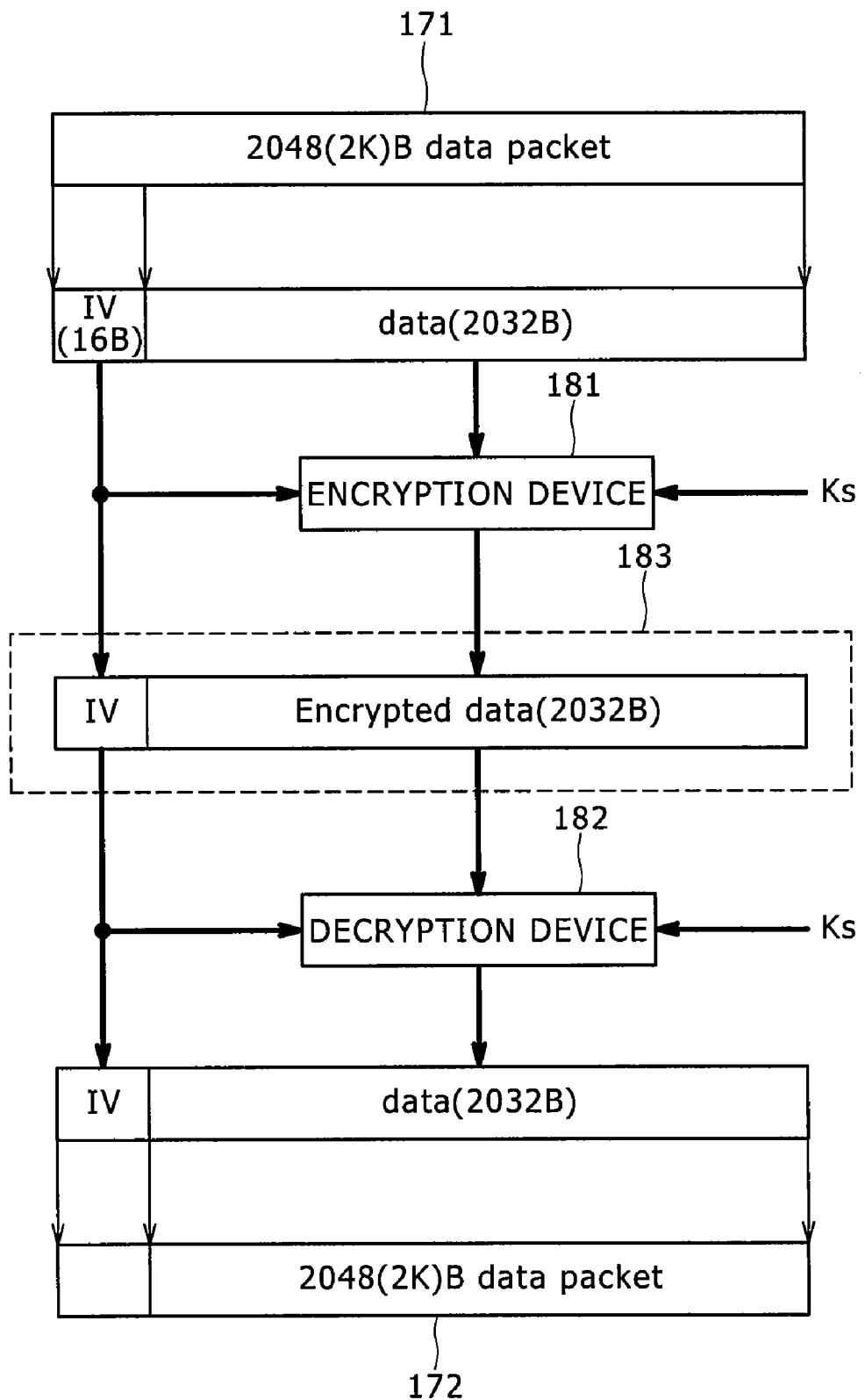
[FIG. 8]
Figure 9:
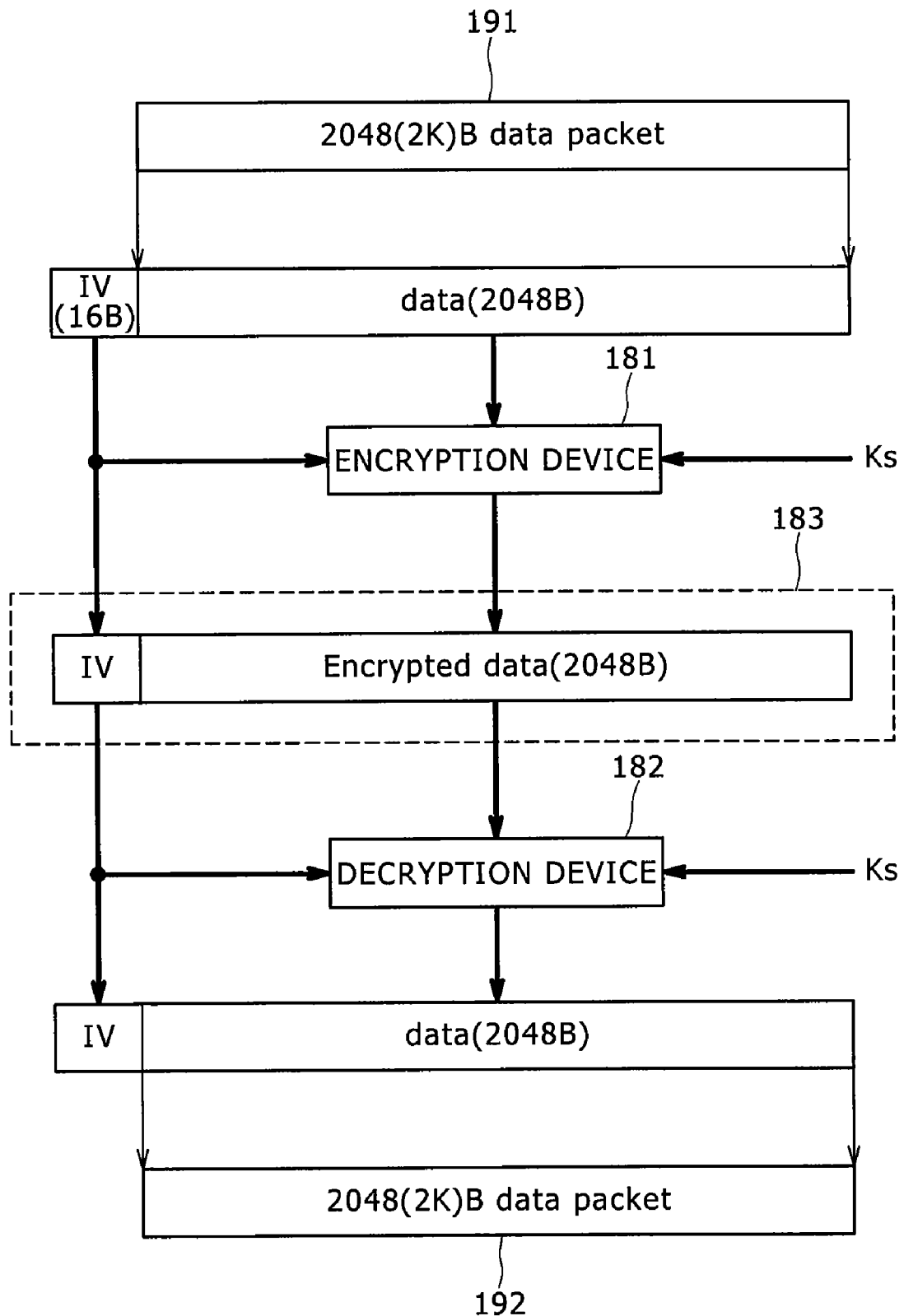
[FIG. 9]

DESCRIPTION OF REFERENCE NUMERALS 301 drive unit, 302 host, 303 disc, 311 authentication processing device, 312 encryption device, 313 sector transfer control device, 314 sector transfer counter, 315 random number generation device, 316 message forwarding device, 317 command processing device, 318 access processing device, 321 authentication processing device, 322 decryption device, 401 drive unit, 402 host, 403 disc, 411 authentication processing device, 412 decryption device, 413 sector transfer control device, 414 sector transfer counter, 415 random number generation device, 416 message forwarding device, 417 command processing device, 418 access processing device, 421 authentication processing device, 422 encryption device.

DETAILED DESCRIPTION

Preferred embodiments of the present invention will now be described. What is described below as the preferred embodiments of the present invention corresponds to the appended claims as follows: the description of the preferred embodiments basically provides specific examples supporting what is claimed. If any example of the invention described below as a preferred embodiment does not have an exactly corresponding claim, this does not means that the example in question has no relevance to the claims. Conversely, if any example of the invention described hereunder has a specifically corresponding claim, this does not mean that the example in question is limited to that claim or has no relevance to other claims.

Furthermore, the description below of the preferred embodiments does not claim to include all examples corresponding to the whole claims. In other words, the description hereunder does not limit or deny any inventive entities which are not covered by the appended claims of the present invention but which may be added or brought about by this applicant in the future by divisional application or by amendment.

According to one preferred embodiment of the present invention, there is provided an information processing apparatus which at least includes: transfer controlling means (e.g., sector transfer control device 313 in FIG. 10 for carrying out step S46 in FIG. 13) for controlling transfer of data; counting means (e.g., sector transfer counter 314 in FIG. 10 for carrying out step S47 in FIG. 13) for counting the number of times the transfer controlling means has controlled the transfer of the data; first determining means (e.g., sector transfer counter 314 in FIG. 10 for carrying out step S45 in FIG. 13) for determining whether the number of times counted by the counting means is at least equal to a predetermined threshold; first instructing means (e.g., sector transfer counter 314 in FIG. 10) which, if the number of times is found at least equal to the threshold by the first determining means, then gives the transfer controlling means an instruction to stop the transfer of the data; generating means (e.g., random number generation device 315 in FIG. 10 for carrying out step S41 in FIG. 13) for generating an initializing vector for use in either encrypting or decrypting the data of which the transfer is controlled by the transfer controlling means; second determining means (e.g., command processing device 317 in FIG. 10 for carrying out step S40 in FIG. 13) for determining whether an instruction to have the initializing vector supplied is given by an external apparatus to and from which is sent and received the data of which the transfer is controlled by the transfer controlling means; and second instructing means (e.g., random number generation device 315 in FIG. 10 for carrying out step S42 in FIG. 13) which, if the instruction to have the initializing vector supplied is found given by the second determining means, then gives the generating means an instruction to generate the initializing vector while giving the counting means an instruction to reset the number of times having been counted.

Preferably, the information processing apparatus of the present invention may further include outputting means (e.g., message forwarding device 316 in FIG. 10 for carrying step S48 in FIG. 13) which, if the instruction is given by the first instructing means, then outputs to the external apparatus a message saying that the transfer of the data is stopped.

The preferred embodiments of the present invention will now be described with reference to the accompanying drawings.

First Embodiment

Figure 10:
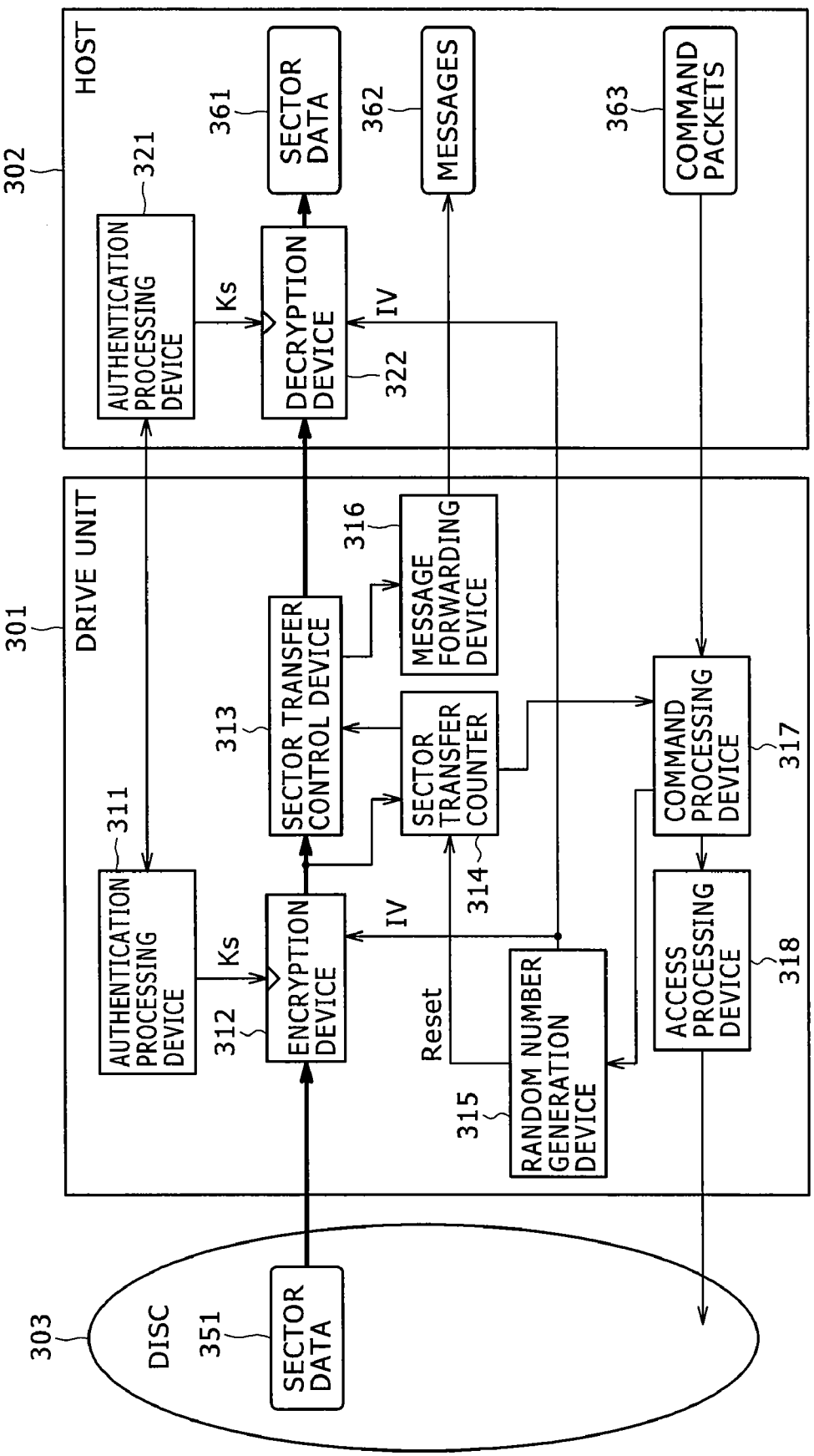
[FIG. 10]

FIG. 10 is a block diagram of a system practiced as the first embodiment of the present invention.

The system shown in FIG. 10 is a system that reproduces (i.e., reads out) data recorded on a recording medium. The system of FIG. 10 is constituted by a drive unit 301 that supplies data and by a host 302 that receives the supplied data.

A disc 303 is any one of such recording media as CD-ROM (Compact Disc-ROM), CD-R (Compact Disc-Recordable), CD-RW (Compact Disc-ReWritable), DVD-ROM (Digital Versatile Disc-ROM), DVD-R (Digital Versatile Disc-Recordable), DVD-RW (Digital Versatile Disc-Rerecordable), DVD+R (DVD+Recordable), DVD+RW (DVD+ReWritable), DVD-RAM (Digital Versatile Disc-Random Access Memory), and Blu-Ray Disc. The scope of the present invention is not limited to these recording media and is applicable to other systems for handling other types of recording media (in terms of recording method or medium shape).

The drive unit 301 and host 302 are interconnected via a suitable interface for sending and receiving data between the drive unit 301 and host 302. The interface may illustratively be ATAPI (AT Attachment with Packet Interface). ATAPI is an interface based on a data transfer protocol for connecting a CD-ROM drive or other peripherals other than the hard disc drive to an IDE (Integrated Drive Electronics) and an ATA (AT Attachment) interface. Illustratively, an ATAPI setup turns SCSI-compliant commands into packets for transfer to an IDE (Integrated Drive Electronics) interface so as to control peripherals. Similar command packets may also be used in conjunction with such physical interfaces as USB (Universal Serial Bus) or IEEE 1394.

The drive unit 301 includes an authentication processing device 311, an encryption device 312, a sector transfer control device 313, a sector transfer counter 314, a random number generation device 315, a message forwarding device 316, a command processing device 317, and an access processing device 318.

The host 302 includes an authentication processing device 321 and a decryption device 322.

The authentication processing device 311 in the drive unit 301 and the authentication processing device 321 in the host 302 authenticate one another.

Under control of the access processing device 318, the encryption device 312 is supplied with sector data 351 read from the disc 303 and with a session key Ks from the authentication processing device 311. The encryption device 312 is also fed with a random number generated by the random number generation device 315 as an initializing vector IV.

The random number generated by the random number generation device 315 may be used unmodified as the initializing vector IV. Alternatively, arrangements may be devised so as to derive the initializing vector IV from both the random number and other data (e.g., PSN (Physical Sector Number) read from the disc 303). Such arrangements may be installed inside the drive unit 301.

The encryption device 313 encrypts the supplied sector data 351 using the session key Ks and initializing vector IV and sends the encrypted data to the sector transfer control device 313. The sector transfer control device 313 transfers the encrypted sector data 351 to the decryption device 322 in the host 303. That is, the data supplied from the drive unit 301 to the host 303 is the encrypted sector data 351.

The encryption device 312 also outputs the data to the sector transfer counter 314. The sector transfer counter 314 is structured so as to count the number of sector data output to the host 302 (i.e., sector data 351 output from the encryption device 312). In other words, the sector transfer counter 314 counts the number of times the sector transfer control device 313 has controlled the transfer of sector data.

The sector transfer counter 314 manages a predetermined maximum count (called Nmax). In operation, the sector transfer counter 314 checks continuously to see if the number of sectors being counted (counter value N) is in excess of the predetermined maximum count.

If the sector count is found to be at least equal to the maximum count (N≧Nmax), the sector transfer counter 314 gives the sector transfer control device 313 an instruction to stop outputting the sector data 351 to the host 302. At the same time, the sector transfer counter 314 gives the command processing device 317 an instruction to stop the access processing device 318 from accessing the disc 303.

Given the instruction to stop outputting the sector data 351 from the sector transfer counter 314, the sector transfer control device 313 gives the message forwarding device 316 an instruction to output a message 362 (an error message in this case) to the host 302.

Meanwhile, the decryption device 322 in the host 303 is supplied with the encrypted sector data 351 from the drive unit 301 through an interface. The decryption device 322 is also fed with the initializing vector IV generated by the random number generation device 315, the vector IV being sent over a route different from the one transporting the sector data 351 (more about this arrangement will be discussed later with reference to FIG. 11).

The decryption device 322 carries out its decryption process using the session key Ks fed from the authentication processing device 331 and the initializing vector IV sent from the drive unit 301. Through this process, the decryption device 322 generates sector data 361.

The host 302 supplies the drive unit 301 with command packets 363 as needed. The command packets 363 include illustratively a Read command giving an instruction to read data from the disc 303, a Write command giving an instruction to write data to the disc 303, and a Report Key command giving an instruction to issue the initializing vector IV.

Figure 11:
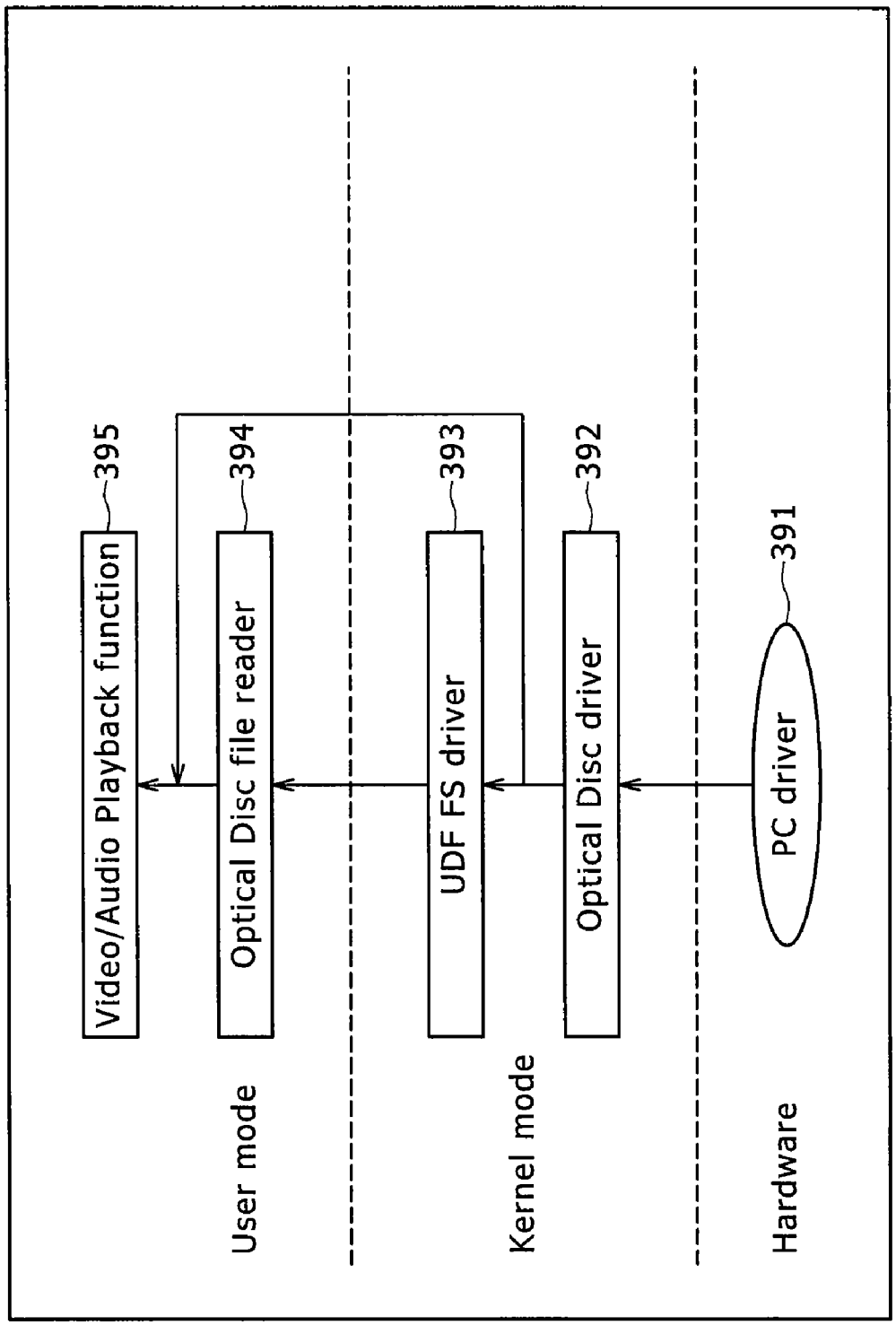
[FIG. 11]

Described below with reference to FIG. 11 are the route over which the sector data 351 is sent and received and the route over which other data is transmitted and received. In FIG. 11, a PC driver 391 is a driver that controls generation of the initializing vector IV, generation of encrypted sector data, and creation of transfer sector data. The data coming from the PC driver 391 is handed over to an Optical Disc driver 392.

The Optical Disc driver 392 is a driver that controls the write and read operations of data to and from an Optical Disc. If the Optical Disc is a recording medium such as DVD, data (i.e., file) is written to that disc in UDF (Universal Data Format). Thus the data (file) retrieved (i.e., controlled) by the Optical Disc driver 392 is transferred to a Video/Audio Playback function 395 via an Optical Disc file reader 394 under control of a UDF FS driver 393.

The Video/Audio Playback function 395 illustratively controls acquisition of transfer sector data, acquisition of the initializing vector IV, and decryption of encrypted sector data.

Video and audio data including sector data are thus sent and received through the UDF FS driver 393 as described. Other data such as the initializing vector IV and the command for getting the vector IV issued are transmitted and received not via the UDF FS driver 393 but through another route such as the so-called SCSI PASS Through under Microsoft Windows (registered trademark).

Of the lines drawn in FIG. 10 between the drive unit 301 and the host 302, the thick line denotes the route over which data is sent and received through the UDF FS driver 393 (called the UDF route hereunder where appropriate); the thin lines represent the route over which data is transmitted and received otherwise (via the SCSI PASS Through; called the pass route hereunder where appropriate).

As shown in FIG. 10, the route connecting the sector transfer control device 313 with the decryption device 322 is the UDF route. The data needed for the process of authentication between the authentication processing device 311 and the authentication processing device 321 is sent and received over the pass route. The message output from the message forwarding device 316 is also transmitted and received over the pass route. Furthermore, the initializing vector IV is exchanged over the pass route.

The UDF FS driver 393 handles data in increments of 2,048 bytes or an integer multiple of 2,048 bytes. That is, the UDF route allows only the data in increments of 2,048 byes or an integer multiple of 2,048 bytes to pass through.

On the other hand, the pass route is basically capable of letting data be sent and received regardless of the data size. In this respect, the pass route is fit for having the 16-byte initializing vector IV sent and received.

How the drive unit 301 shown in FIG. 10 works will now be described in reference to the flowcharts of FIGS. 12 and 13. In step S31, a check is made to determine whether the disc 303 is loaded into the drive unit 301. If in step S31 the disc 303 is found loaded in the drive unit 301, step S32 is reached. In step S32, a check is made to determine whether a predetermined application is started up by the host 302.

The predetermined application is an application needed to write or read data to or from the disc 303 loaded in the drive unit 301.

If in step S32 the predetermined application is found started up by the host 302, step S33 is reached. In step S33, the drive unit 301 and the host 302 authenticate one another and a session key Ks is generated by the drive unit 301 and the host 302 (for shared use). In step S34, a check is made to determine whether generation of the session key Ks is completed. Steps S33 and S34 are repeated until the generation of the session key Ks is found to be complete.

If in step S34 the generation of the session key Ks is found complete, step S35 is reached. In step S35, the counter value N on the sector transfer counter 314 in the drive unit 301 is set for a number Nmax that is a maximum counter value (i.e., N=Nmax).

After the counter value N is set for Nmax, the sector transfer counter 314 gives an instruction to inhibit the output of data from the sector transfer control device 313 to the host 302.

In step S36, a check is made to determine whether the host 302 has made a request to have the initializing vector IV transferred. The check is accomplished by the command processing device 317 determining whether a command packet 363 is received from the host 302 and whether the received command packet 363 represents the request to have the initializing vector IV transferred.

Step S36 is repeated until the request to have the initializing vector IV transferred is detected. When the initializing vector transfer request is found to be made in step S36, step S37 is reached. In step S37, the initializing vector IV is generated.

More specifically, the request to have the initializing vector IV transferred is detected by the command processing device 317 receiving the command packet 363 from the host 302 and analyzing it to see if it represents the request in question. Once the request is detected, the command processing device 317 notifies the random number generation device 315 of detecting the request. Given such notification, the random number generation device 315 generates the initializing vector IV in step S37.

The random number generation device 315 generates a random number that may be either used unmodified as the initializing vector IV, or XORed with predetermined information (e.g., information contained in the command packet 363 requesting the transfer of the initializing vector IV) so as to generate the initializing vector IV.

Besides generating the initializing vector IV, the random number generation device 315 gives the sector transfer counter 314 an instruction to reset the counter value N to zero. Upon receipt of the instruction, the sector transfer counter 314 initializes the counter value N to zero in step S38. When the counter value N is initialized to zero on the sector transfer counter 314, the sector transfer control device 313 is switched to the state that authorizes the output of data.

In step S39, the initializing vector IV generated by the random number generation device 315 is supplied to the host 302. Because the initializing vector IV is placed (i.e., transferred) on the pass route, the initializing vector IV can be sent and received between the drive unit 301 and the host 302 even if the initializing vector is 16 bytes long.

The sending and receiving of the initializing vector IV taking place between steps S33 and S39 will now be described in more detail with reference to FIG. 14.

The host 302 and the drive unit 301 authenticate one another in steps S101 and S11, respectively. Control is passed on to the next step only after a successful completion of the mutual authentication. Following the mutual authentication, the authentication processing device 311 in the drive unit 301 and the authentication processing device 321 in the host 302 generate the session key Ks each (for shared use).

In step S102, the host 302 generates a command packet 363 and outputs it to the drive unit 301. The command packet 363 generated and output in step S102 constitutes a REPORT KEY command which, in this example, requests transfer of an initializing vector IV.

In step S112, the drive unit 301 receives the REPORT KEY command. In step S113, the drive unit 301 generates the initializing vector IV. In step S114, the drive unit 301 outputs the generated initializing vector IV to the host 302. The initializing vector IV is output unmodified to the host 302.

In step S103, the host 303 receives the initializing vector IV output from the drive unit 301.

The initializing vector IV may be transferred unmodified from the drive unit 301 to the host 302 as described. Alternatively, the initializing vector IV may be encrypted when output to the host 302.

The initializing vector IV is a randomly changing number because it is generated by the random number generation device 315 using a random number. Unlike the session key Ks, the initializing vector IV does not need to be concealed in particular. For that reason, the initializing vector IV may be transferred in unencrypted form as described above with reference to FIG. 14.

Still, there does exist an obvious precondition recommending that the initializing vector IV be preferably unpredictable. It is preferred that the precondition be met by encrypting the initializing vector IV prior to its transfer so as to improve security.

Figure 14:
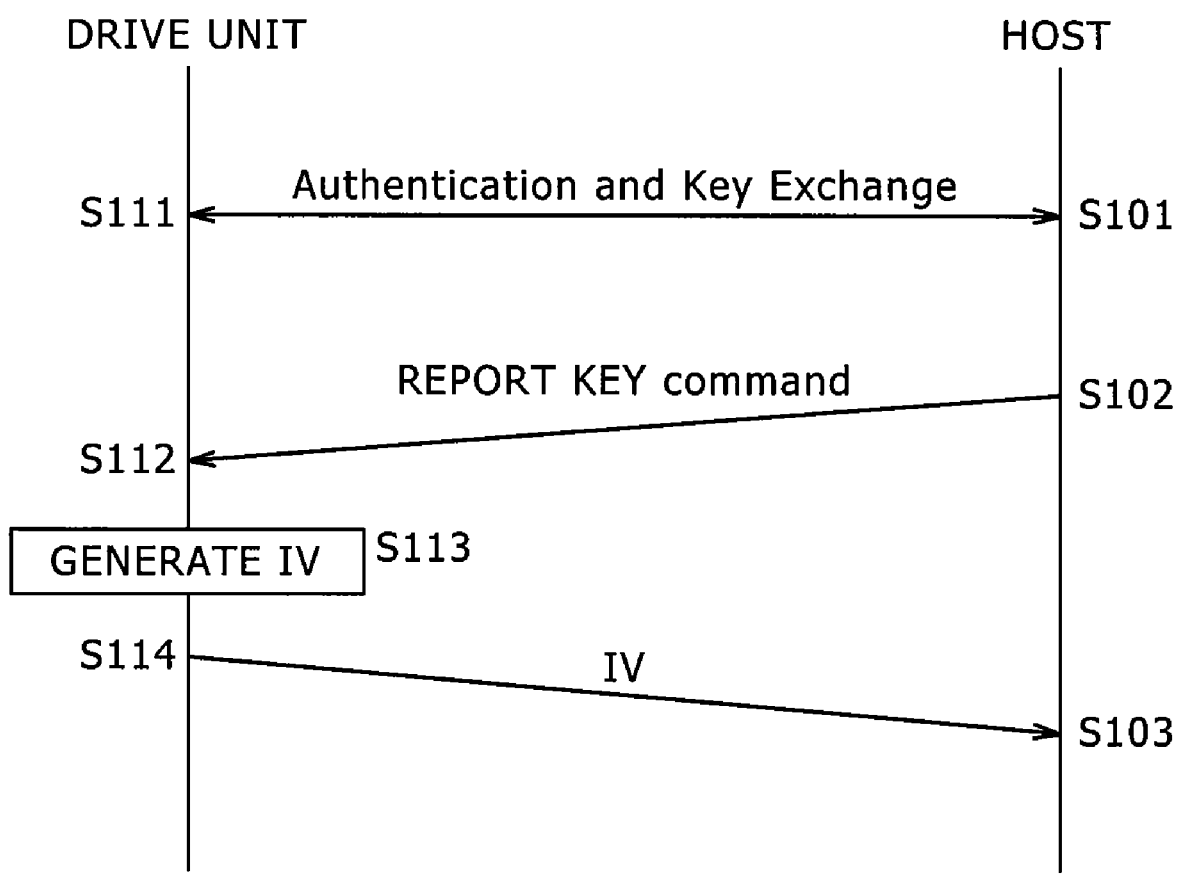
[FIG. 14]
Figure 15:
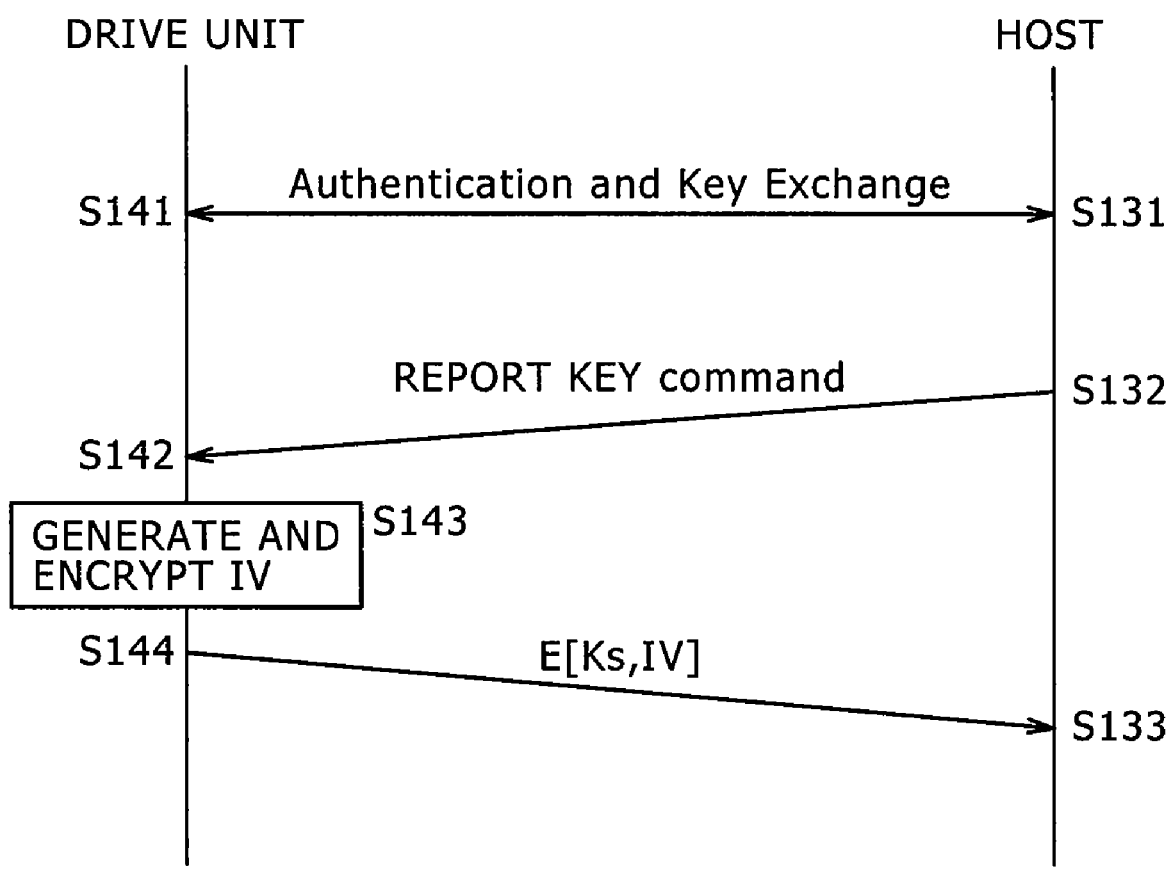
[FIG. 15]

If the initializing vector IV is to be encrypted for higher security before being transferred, the steps involved take place as shown in FIG. 15. On the side of the host 302, steps S131 to S133 are carried out basically in the same manner as steps S101 to S103 in FIG. 14. The difference is that the initializing vector IV received in step S103 needs to be decrypted upon receipt because it has been encrypted.

On the side of the drive unit 301, steps S141 to S144 are performed basically in the same manner as steps S11 to S114 in FIG. 14. The difference is that following its generation in step S143, the initializing vector IV is encrypted using the session key Ks and the encrypted initializing vector IV (E[Ks, IV]) is transferred to the host 302 in step S144.

When the host 302 issues a request to have the initializing vector IV transferred, the drive unit 301 generates the initializing vector IV as described and transfers it to the host 302. Needless to say, the drive unit 301 transfers the generated initializing vector IV not only to the host 302 but also to the encryption device 312 (FIG. 10) inside the drive unit 301.

Figure 12:
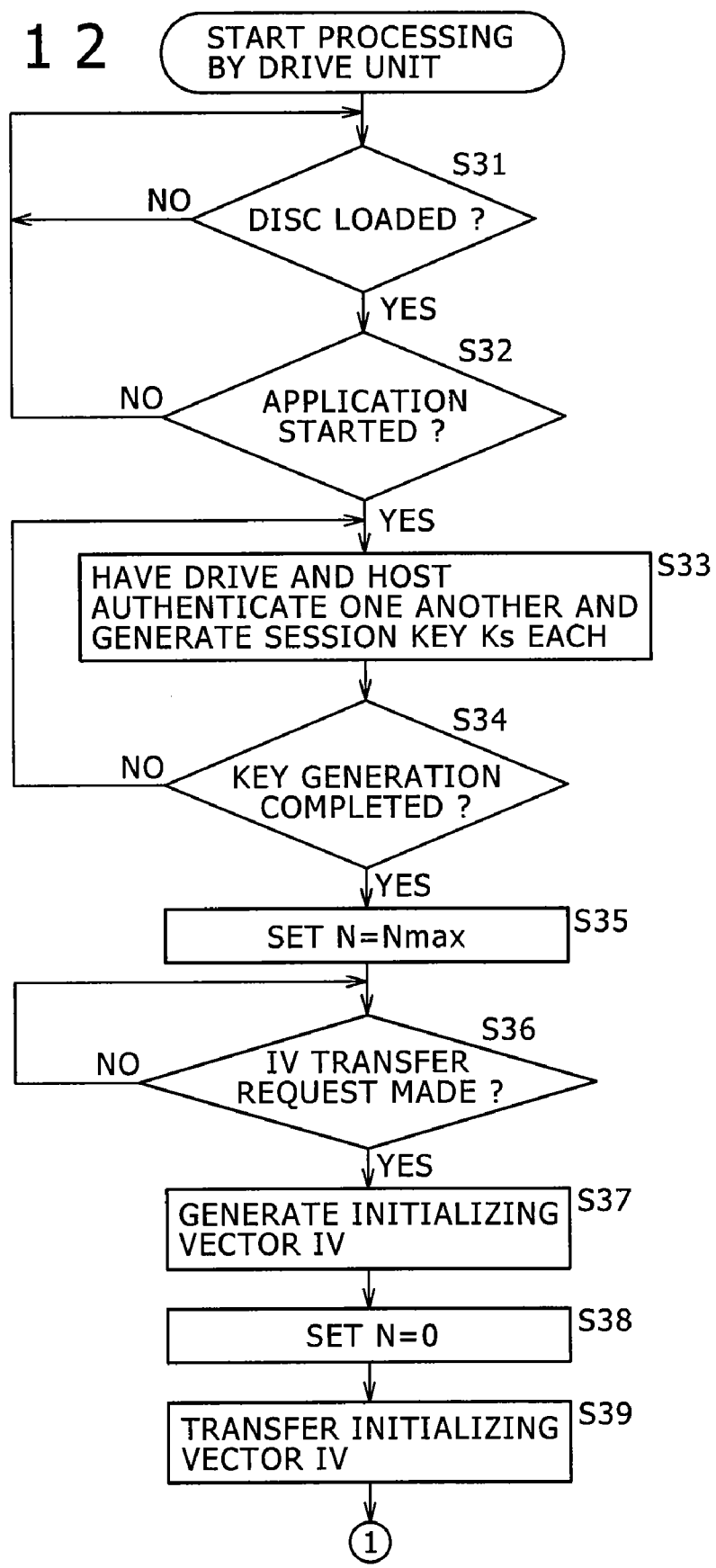
[FIG. 12]

Returning to the description of the flowchart of FIG. 12, step S40 (FIG. 13) is reached upon completion of the transfer of the initializing vector IV in step S39. In step S40, a check is made to determine whether a request is made to have the initializing vector IV issued again. If in step S40 the initializing vector reissue request is found to be made, steps S41 to S43 are carried out.

Figure 16:
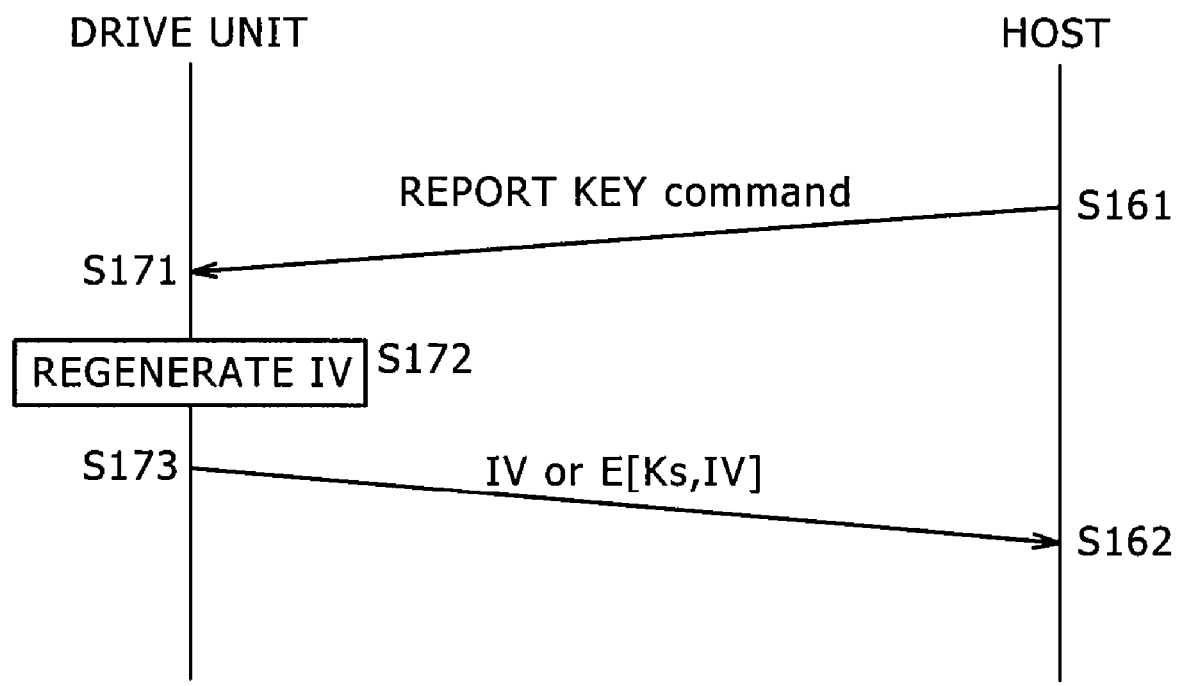
[FIG. 16]

Steps S41 to S43 are basically the same as steps S37 to S38. More about this part of the process is explained below with reference to FIG. 16. In step S161, the host 301 requests the drive unit 301 to reissue the initializing vector IV. The reissue request is made in the form of a command packet 363 being output. Illustratively, the command packet 363 is the same as the REPORT KEY command issued in step S102 of FIG. 14.

In step S171, the drive unit 301 receives the REPORT KEY command. In step S172, the drive unit 301 generates the initializing vector IV again. Regeneration of the initializing vector IV is carried out in the same manner as in step S113 of FIG. 14 or in step S143 of FIG. 15. The initializing vector IV again generated is transferred to the host 302 in step S173. The initializing vector IV may be transferred either encrypted or unmodified.

Figure 13:
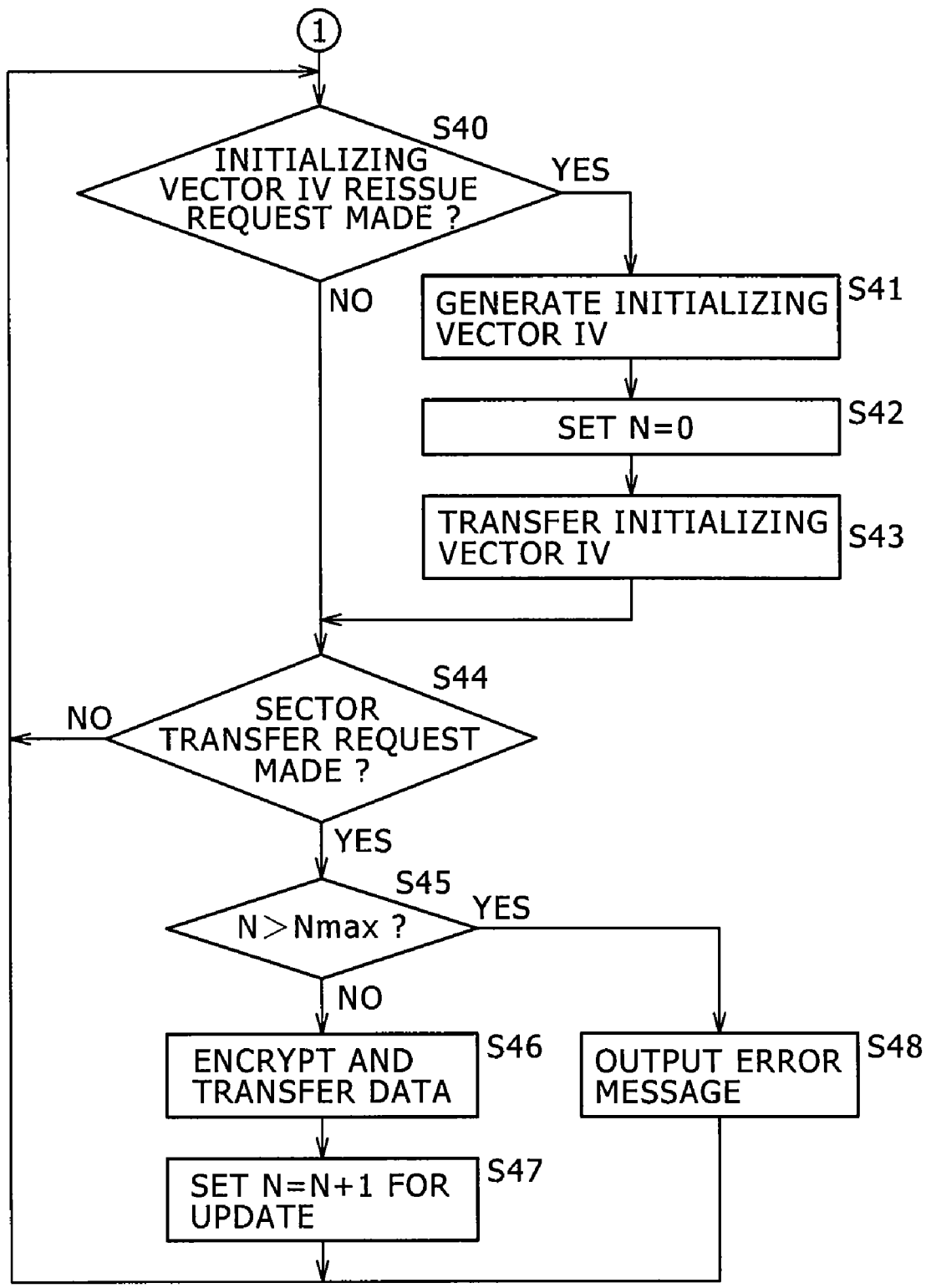
[FIG. 13]

Returning to the description of the flowchart of FIG. 13, step S44 is reached if the request to have the initializing vector IV reissued is not detected in step S40 or if the processing associated with transfer of the initializing vector IV is completed in step S43.

In step S44, a check is made to determine whether a request is made for the transfer of sector data 351. The check is accomplished by the command processing device 317 determining whether the command packet 363 is received from the host 302 and whether the received command packet 363 constitutes a request for the transfer of the sector data 351.

If in step S44 the request for the transfer of the sector data 351 is not detected, step S40 is reached again and the subsequent steps are repeated. If the request for the transfer of the sector data 351 is detected in step S44, step S45 is reached.

In step S45, a check is made to determine whether the counter value N on the sector transfer counter 314 is larger than the count Nmax (i.e., condition of N>Nmax) If in step S45 the counter value N is not found larger than the count Nmax, step S46 is reached. As long as the counter value N remains smaller than the count Nmax (i.e., the condition of N<Nmax is met), the sector transfer control device 313 is authorized to output data (i.e., allowed to transfer data to the host 302).

In step S46, the sector transfer control device 313 transfers data to the host 302. More specifically, under instructions from the command processing device 317, the access control device 318 controls reading of the sector data 351 from the disc 303. Under control of the access control device 318, the sector data 351 read from the disc 303 is supplied to the encryption device 312.

The encryption device 312 encrypts the sector data 351 using the session key Ks fed from the authentication processing device 311 and the initializing vector IV coming from the random number generation device 315. The encrypted sector data 351 is transferred to the host 302 under control of the sector transfer control device 313. In this case, the sector data 351 is transferred over the UDF route in increments of 2,048 bytes (or an integer multiple of 2,048 bytes).

When the data is output from the encryption device 312, the sector transfer counter 314 is notified thereof. In step S47, the sector transfer counter 314 updates the counter value N to be managed by incrementing the value N by 1 (N+1), and establishes the updated value as a new counter value N. After the updating of the counter value N on the sector transfer counter 314, step S40 is reached again and the subsequent steps are repeated.

More about the transfer of the sector data 351 will now be discussed by referring to the timing chart of FIG. 17. In step S201, the host 302 issues a READ command. This is a command that is issued to read the sector data 351 from the disc 303. A WRITE command will be issued upon writing of data to the disc 303, as will be described later.

The READ command issued here is one type of command packet 363 having illustratively the data structure shown in FIG. 18. More details of the command are found in INCITS T10 WORKING DRAFT "Multimedia Command Set-4 (MMC-4)."

The command packet 363 shown in FIG. 18 represents the format of the READ or WRITE command. Of the data fields in the command packet 363 indicated in FIG. 18, those that are needed in the ensuing description will be explained here.

An "Operation Code" field is a field that accommodates data indicating whether this command is the READ command or the WRITE command. Referencing the data written in this field thus allows the drive unit 301 having received the command from the host 302 to determine whether the received command is the READ command or the WRITE command. The "Operation Code" field holds 1 byte data.

A "Logical Block Address" field is a field that accommodates the starting LBA of the location from which to start reading data. If the command packet 363 constitutes the WRITE command, the starting LBA of the location to which to start writing data is placed in this field. The "Logical Block Address" field holds 4 byte data.

A "Transfer Length" field is a field which accommodates either data for designating the number of sectors to be read if the command packet 363 is the READ command, or data for designating the number of sectors to be written if the command packet 363 is the WRITE command. The "Transfer Length" field holds 4 byte data.

The command packet 363 issued by the host 302 in step S201 is a command in which the "Operation Code" field has the value designating the READ command. It is assumed here that the "Transfer Length" field included in the issued READ command contains "N1."

The READ command issued in step S201 is supplied to the command processing device 317 of the drive unit 301 in step S231. The command processing device 317 references the "Operation Code" field in the supplied command and recognizes that this is the READ command. The command processing device 317 then references the "Logical Block Address" field to recognize the address from which to start reading data, and references the "Transfer Length" field to find that "Transfer Length"=N3 in this case.

The command processing device 317 sends the result of the recognition to the access processing device 318. Based on the recognition result given by the command processing device 317, the access processing device 318 controls reading of data from the disc 303. The access processing device 318 illustratively carries out address translation.

More specifically, the access processing device 318 performs LBA/PSN translation. LBA stands for "Logical Block Address" and PSN for "Physical Sector Number". LBA designates a logical address and is included illustratively in the READ command. This is a logical address that can be handled in common by both the drive unit 301 and the host 302 in a manner independent of the physical medium of the disc 303 from which to read data.

As opposed to LBA, PSN designates a physical address. Although the command packet 363 includes LBA, this address only represents a logical address on the disc 303; an actual physical address PSN read from the disc 303 is translated into a suitable logical address as needed for common use between the two sides. The translation from the physical address (PSN) to the logical address (LBA) or vice versa is carried out by the access processing device 318.

Illustratively, logical sectors having sequential logical sector numbers are allotted consecutively to the physical sectors constituting the user data area (not shown), a recording area made available for the user, in reference to a physical sector having a particular physical sector number on the disc 303. Examples of the above-mentioned address translation are described in INCITS T10 WORKING DRAFT "Multimedia Command Set-4 (MMC-4)."

Following the translation from LBA to PSN, a search is made in step S232 for that location on the disc 303 which is designated by the translated PSN. Following the search, the pickup (not shown) is moved to the location from which to read data and other related operations are carried out so that the sector data 351 is read from the disc 303. The sector data 351 thus retrieved is supplied to the encryption device 312.

The encryption device 312 is fed with the session key Ks from the authentication processing device 311 as well as the initializing vector IV from the random number generation device 315. The encryption device 312 proceeds to encrypt the sector data 351 using the supplied session key Ks and initializing vector IV. The encrypted sector data 351 (Encrypted Sector Data #1 in this example) is output to the decryption device 322 of the host 302 in step S232 under control of the sector transfer control device 313.

The decryption device 322 decrypts the supplied Encrypted Sector Data #1 through the use of the session key Ks fed from the authentication processing device 321 and the initializing vector IV coming from the random number generation device 315 of the drive unit 301. The sector data 361 generated in this manner is sent to application software, to the display unit, or to speakers, not shown.

The above steps are repeated between the drive unit 301 and the host 302. A series of Physical Sector Data is read by the drive unit 301. That is, a sequence of sector data is read from the disc 303 under seek control of the drive unit 301 and supplied to the drive unit 301.

In steps S233 through S240, the drive unit 301 encrypts the retrieved sector data consecutively and supplies the encrypted data to the host 302 on request (i.e., in response to the issued READ command).

On transferring the sector data to the host 302, the drive unit 301 updates concurrently the counter value N managed by the sector transfer counter 314. Illustratively, when the sector data 351 is encrypted and transferred to the host 302 in step S232, the counter value N on the sector transfer counter 314 is incremented by 1 for an update (as carried out in step 47). As the update of the counter value N is repeated (i.e., as the sector data is transferred consecutively to the host 302), there comes a time when the counter value N becomes larger than the threshold Nmax (i.e., condition of N>Nmax is met).

Figure 17:
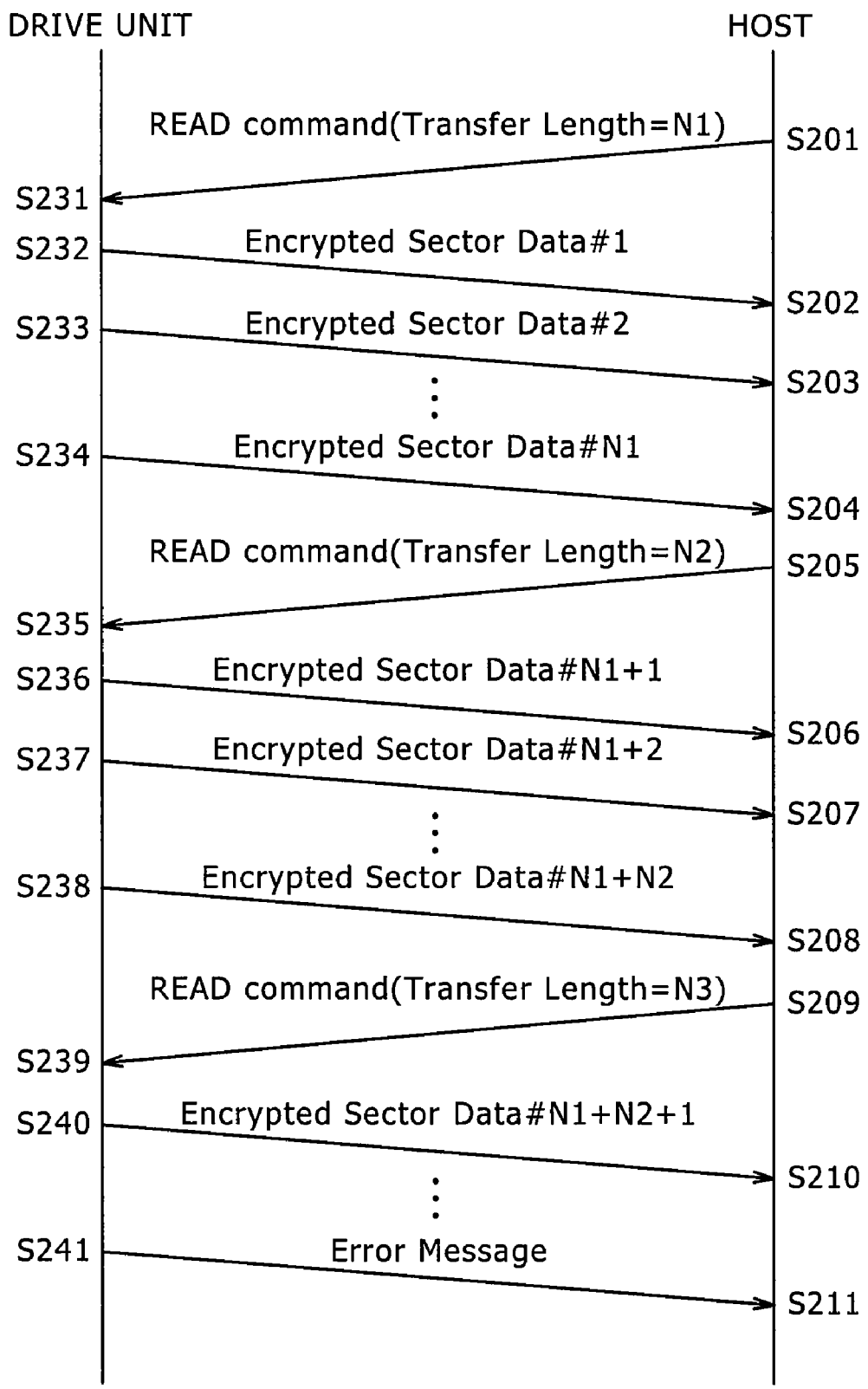
[FIG. 17]

In reference to FIG. 17, suppose that settings are made so that (N1+N2)<Nmax<(N1+N2+N3). In that case, after the (N1+N2+1)th sector data is output in step S240 (i.e., after the counter value N managed by the sector transfer counter 314 has reached (N1+N2+1)), sector data is read successively from the disc 303, and encrypted and transferred repeatedly. With the counter value N incremented by 1 repeatedly, the condition of N>Nmax is eventually met.

When the condition of N>Nmax is met, i.e., when the result of the check in step S45 (FIG. 13) is affirmative ("YES"), step S48 is reached (step S241 in FIG. 17).

In step 48 (in step S241), the drive unit 301 outputs an Error Message to the host 302. If the sector transfer counter 314 in the drive unit 301 finds the counter value N it is counting to be larger than the threshold Nmax, the sector transfer counter 314 gives the sector transfer control device 313 an instruction to keep the data sent by the encryption device 312 from getting output to the host 301.

Given the output stop instruction from the sector transfer counter 314, the sector transfer control device 313 stops outputting the sector data and notifies the message forwarding device 316 that the output stop instruction has been received. Upon receipt of that notification from the sector transfer control device 313, the message forwarding device 316 creates an error message and sends it to the host 302. This error message brings the host 302 to recognize that the designated data cannot be supplied.

The message represents the state in which the drive unit 301 does not output data. In other words, the state in which data output was authorized as a result of the successful completion of the authentication process by the drive unit 301 is now canceled, and no data is allowed to be output.

The embodiment described above thus makes it possible to change the state that has been established so as to authorize data output. Following the output of the error message, the host 302 may issue an instruction to have data read from the disc 303 but no data will be read in response to that instruction.

After the error message is output, the transmission of data from the drive unit 301 to the host 302 is halted. In order to avoid getting the data output stopped this way, the host 302 need only request the drive unit 301 to issue the initializing vector IV in a suitably timed manner.

More specifically, requesting the initializing vector IV to be issued (e.g., in step S40 of FIG. 13) resets the counter value N on the sector transfer counter 314 to zero (in step S42). This prevents the condition of N>Nmax from being met, whereby the output of the error message (in step S48) is averted.

The host 302 periodically requests that the initializing vector IV be issued. Making the request periodically signifies illustratively that following each request for the issue of the initializing vector IV, another request for the initializing vector IV issue is made when the accumulated amount of data to be transferred is found to exceed a predetermined data quantity (e.g., 16 Mbytes (or 8K sectors)). Alternatively, following each request to have the initializing vector IV issued, another request for IV issue is made upon elapse of a predetermined time period.

In any case, the host 302 requests that the initializing vector IV be issued in a suitably timed manner. While the process is being performed normally (i.e., legitimately), the drive unit 301 carries out steps S41 to S43 periodically. This causes the counter value N on the sector transfer counter 314 to be reset to zero periodically.

The measures taken as described above solve at least the following problems: once the drive unit 301 and the host 302 have authenticated one another, the drive unit 301 outputs protected data to the receiving party (e.g., application started up by the host 302) as instructed by the party regardless of the party being legitimate or not. Another problem is that the bus connecting the two sides might be tapped by a third party who might steal data from the bus and decrypt the misappropriated data (for illicit use).

The above problems are resolved as described, i.e., first by having the protected data (i.e., sector data 351 recorded on the disc 303) encrypted using the session key Ks before the transfer of the data from the drive unit 301 to the host 302 through the bus. This makes it difficult for an unscrupulous third party tapping the bus for data theft to decrypt the pilfered data in protected form into plain text data.

Furthermore, the data of interest is encrypted through the use of the initializing vector IV which is randomly changed using random numbers. This makes it much more difficult for the third party having somehow stolen the protected data to decrypt it into plain text data.

Having the initializing vector IV varied makes it difficult for the third party to determine whether the target plain text data is special data. This contributes to forestalling data substitution, falsification, or other data abuses. With the initializing vector IV suitably updated, it is possible to circumvent the problem of turning an encryption key (i.e., session key Ks) easily predictable where that single key is used to encrypt a large quantity of data.

According to this embodiment, as described above, the supply of data is stopped unless the host 302 issues instructions to have the initializing vector IV suitably updated. It is thus possible to bypass the problem of letting the drive unit 301 output protected data to the host 302 once the two sides have authenticated one another, regardless of whether the receiving party (e.g., application started up by the host 302) is legitimate or not.

That is, the legitimate drive unit 301 is controlled so as to transfer protected data only to the legitimate host 302.

Whereas the embodiment above was shown to have the initializing vector IV updated, it is possible alternatively to have the session key Ks updated for encryption use. In other words, the host 302 may issue not the instruction to have the initializing vector IV issued repetitively but the instruction to have the session key Ks issued repeatedly.

Still, since the session key Ks is generated only after the successful completion of the process of mutual authentication, it may be preferable to have the initializing vector IV updated in view of the processing time and performance that would be required to update the session key Ks.

Although the embodiment above was shown having the target data read (i.e., reproduced) from the disc 303, this does not signify that the scope of the present invention is limited to the reproduction of data. The present invention may also be applied to the writing (i.e., recording) of data to the disc 303.

Figure 19:
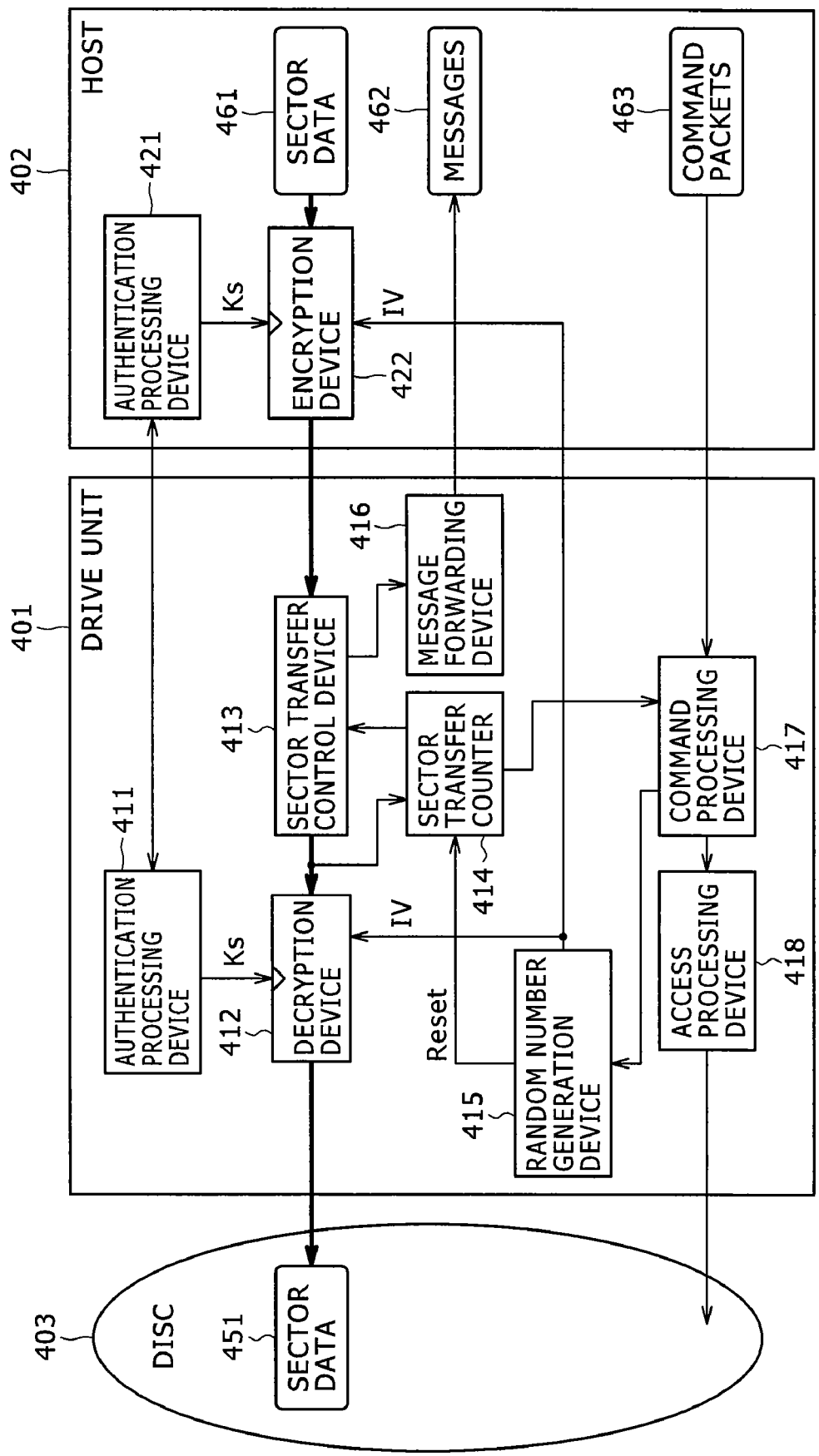
[FIG. 19]

FIG. 19 is a block diagram of a typical system configuration in effect when the present invention is applied to a recording apparatus.

Referring to FIG. 19, a drive unit 401 in the recording apparatus writes data coming from a host 402 to a disc 303 loaded in the drive unit 401. The drive unit 401 includes an authentication processing device 411, a decryption device 412, a sector transfer control device 413, a sector transfer counter 414, a random number generation device 415, a message forwarding device 416, a command processing device 417, and an access processing device 418.

The host 402 includes an authentication processing device 421 and an encryption device 422.

The structure of the recording apparatus shown in FIG. 19 is substantially the same as the structure of the reproducing apparatus indicated in FIG. 10 and thus will not be described further in detail. Only the major structural differences between the two apparatuses are discussed below.

In the recording apparatus of FIG. 19, sector data 451 is recorded to the disc 403. The sector data 451 to be recorded is constituted by sector data 461 supplied from the host 402. Using the session key Ks provided by the authentication processing device 421, the encryption device 422 of the host 402 encrypts the sector data 461 retrieved from the recording medium or a hard disc drive, not shown.

The sector data 461 encrypted by the encryption device 422 is fed to the sector transfer control device 413. The sector transfer control device 413 forwards the supplied sector data 461 to the decryption device 412. The decryption device 412 decrypts the received sector data 461 by use of the session key Ks supplied from the authentication processing device 411. The sector data 461 thus decrypted is recorded to the disc 403 under control of the access processing device 418.

The sector transfer counter 414 counts the number of sectors output from the sector transfer control device 413 to the decryption device 412. The other components of the recording apparatus are basically the same as their counterparts of the reproducing apparatus shown in FIG. 10 and their workings are substantially the same.

The drive unit 401 of the recording apparatus in FIG. 19 carries out basically the same steps as those in the flowcharts of FIGS. 12 and 13, and thus these steps will not be discussed further. Only the different steps performed by the drive unit 401 are described hereunder by referring again to the flowcharts of FIGS. 12 and 13.

In step S44, the drive unit 401 checks to determine whether there is a request for the recording of sector data. The check is accomplished by the command processing device 417 determining whether a command packet 463 is received from the host 402 and whether the received command packet 463 constitutes the command (i.e., WRITE command) requesting the writing of the sector data 461.

In step S46, the encrypted sector data 461 is supplied to and decrypted by the decryption device 412. The decrypted sector data 461 (451) is written to the disc 403. The other steps are basically the same as those performed by the reproducing apparatus. Unless the host 402 periodically requests that the initializing vector IV be issued, the writing of data by the drive unit 401 is stopped (data output from the host 403 is halted).

The measures above make it possible to prevent the protected data under management of the host 402 to be illicitly output and written to the disc 403.

Figure 20:
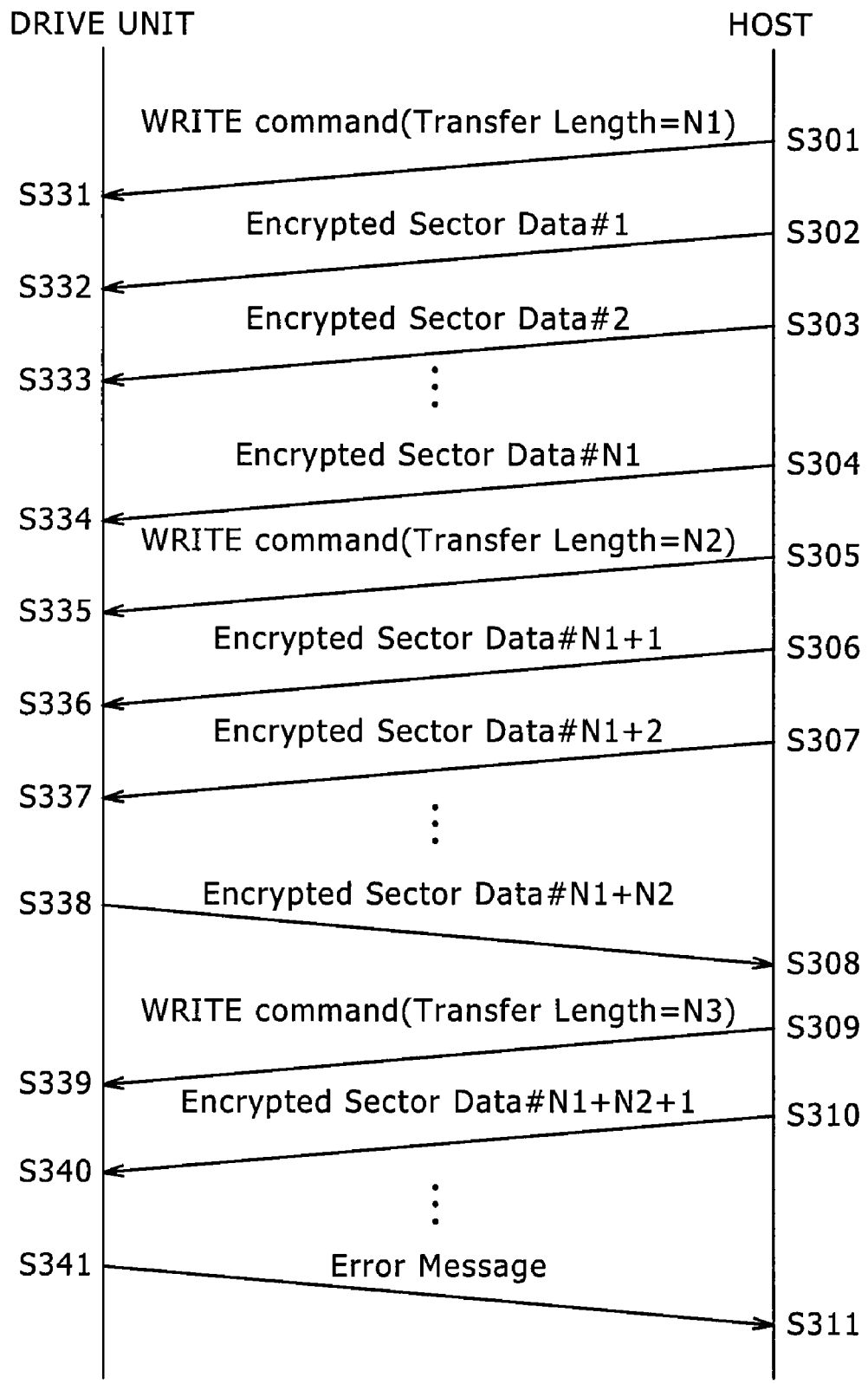
[FIG. 20]

Described below with reference to the timing chart of FIG. 20 are the steps associated with the recording of data by the recording apparatus shown in FIG. 19. The basic processing is the same as that in the timing chart of FIG. 17 and thus will not be discussed further in detail. A major difference is that in step S301, the host 402 sends the WRITE command designating the writing of data.

In step S302, the encryption device 422 of the host 402 encrypts the sector data 461 using the session key Ks, and sends the encrypted data (Encrypted Sector Data #1) to the drive unit 401. The sector transfer control device 423 of the drive unit 401 forwards the supplied Encrypted Sector Data #1 to the decryption device 412.

The decryption device 412 decrypts the supplied data through the use of the session key Ks fed from the authentication processing device 411 and the initializing vector IV provided by the random number generation device 415, thereby generating the sector data 451. The sector data 451 thus generated is written to the disc 403 under control of the access processing device 418.

During the processing above, the sector transfer counter 414 counts the number of sectors output from the sector transfer control device 413, and checks to determine whether the counter value N being counted has become greater than the value Nmax. As the counter value N becomes larger (i.e., as the sector data is output consecutively from the sector transfer control device 413), there comes a time when the counter value N becomes larger than the threshold Nmax (i.e., condition of N>Nmax is met).

In reference to FIG. 20, suppose that settings are made so that (N1+N2)<Nmax<(N1+N2+N3). In that case, after the (N1+N2+1)th sector data is received in step S340 (i.e., after the counter value N managed by the sector transfer counter 414 has reached (N1+N2+1)), sector data is written successively to the disc 403. With the counter value N then incremented by 1 repeatedly, the condition of N>Nmax is eventually met.

When the condition of N>Nmax is met, i.e., when the result of the check in step S45 (FIG. 13) is affirmative ("YES"), step S48 is reached (step S341 in FIG. 20).

In step 48 (in step S341), the drive unit 401 outputs an Error Message to the host 402. If the sector transfer counter 414 of the drive unit 401 finds that the counter value N is larger than the threshold Nmax, the sector transfer counter 414 gives the sector transfer control device 413 an instruction to keep the data from getting output to the decryption device 412.

Given the output stop instruction from the sector transfer counter 414, the sector transfer control device 413 stops outputting the sector data and notifies the message forwarding device 416 that the instruction to stop data output has been received. Upon receipt of that notification from the sector transfer control device 413, the message forwarding device 416 creates an error message and sends it to the host 402. This error message brings the host 402 to recognize that the designated data cannot be written.

The message represents the state in which no data is input from the drive unit 401. That is, the host 402 having received the error message is inhibited from outputting any data in this state.

When the steps above are carried out, the same effects as those offered by the reproducing apparatus described earlier are also provided.

Practicing the present invention in the manner described above helps enhance security in the sending and receiving of data between the drive unit and the host.

In the foregoing description, the reproducing apparatus (FIG. 10) and the recording apparatus (FIG. 19) were each shown and discussed as a separate entity. Alternatively, the reproducing apparatus and recording apparatuse may be housed in the same enclosure. In this case, it is obviously possible for the two apparatuses to share some of their components such as the random number generation device 315 (415) performing the same functions in each apparatus.

Although the examples discussed above were shown adopting the CBC scheme as their encryption and decryption algorithm, this is only an example and not limitative of the present invention. Alternatively, the present invention may be practiced pursuant to the CFB (Cipher Feed Back) scheme, OFB (Output Feed Back) scheme, or other appropriate schemes.

Second Embodiment

The first embodiment described above was shown to have the drive unit 301 (401) generating the initializing vector IV. In the second embodiment of the present invention to be discussed below, the host will be shown to generate the initializing vector IV.

Figure 21:
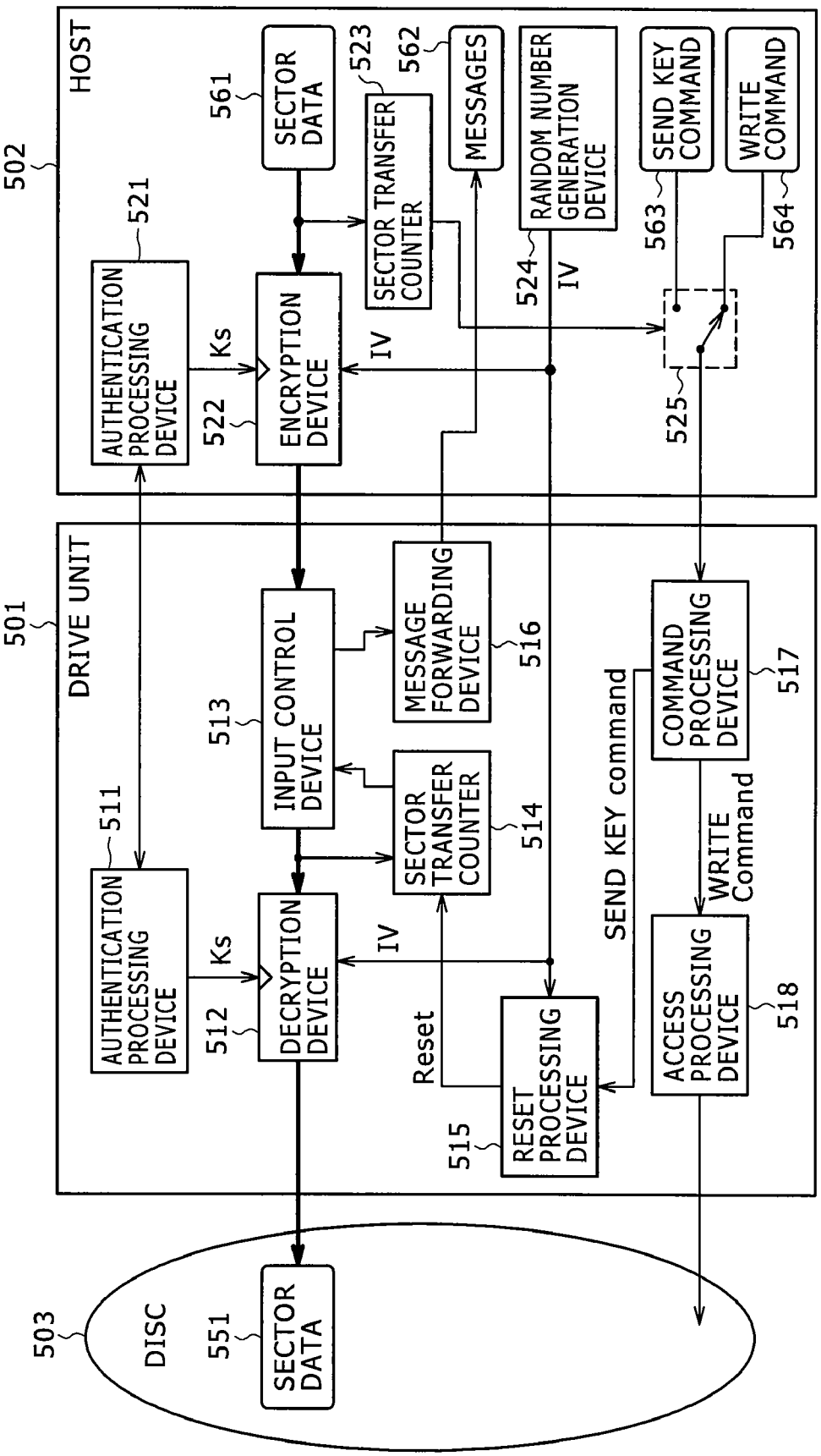
[FIG. 21]

FIG. 21 is a block diagram showing a typical system configuration of the second embodiment according to the present invention. In the system, a drive unit 501 includes an authentication processing device 511, a decryption device 512, an input control device 513, a sector transfer counter 514, a reset processing device 515, a message forwarding device 516, a command processing device 517, and an access processing device 518.

A host 502 in the system includes an authentication processing device 521, an encryption device 522, a sector transfer counter 523, a random number generation device 524, and a switch 525.

In the system shown in FIG. 21, the host 502 supplies encrypted sector data 561 to the drive unit 501. After being decrypted, the sector data 561 is written to a disc 503 as sector data 551.

The authentication processing device 511 in the drive unit 501 and the authentication processing device 521 in he host 502 authenticate one another.

The encryption device 522 in the host 502 is supplied with the sector data 561 to be written to the disc 503 and with the session key Ks sent from the authentication processing device 511. The encryption device 522 is also fed with a random number generated by the random number generation device 524 as the initializing vector IV. Using the session key Ks and initializing vector IV, the encryption device 522 encrypts the supplied sector data 561 and sends it to the drive unit 501.

On receiving the encrypted sector data 561 from the host 502, the input control device 513 in the drive unit 501 transfers the input data to the decryption device 512. The decryption device 512 is also fed with the initializing vector IV generated by the random number generation device 524, the vector IV being sent over a route different from the one transporting the sector data 561. The decryption device 512 carries out its decryption process using the session key Ks fed from the authentication processing device 511 and the initializing vector IV sent from the 502. Through this process, the decryption device 512 generates the sector data 551 (the same data as the sector data 561). The sector data 551 thus generated is written to the disc 503 under control of the access processing device 518.

When the host 502 outputs the sector data 561, the sector transfer counter 523 is arranged to count the number of sectors to be transferred (having been transferred). The switch 525 is set to be changed over depending on the number of sectors thus counted. As will be discussed later in more detail, before the counted number of sectors (called the counter value N hereunder) reaches a predetermined count (called the threshold Nmax hereunder), the SEND KEY command 563 is issued to have the initializing vector IV transferred.

The sector transfer counter 514 is also provided in the drive unit 501. The sector transfer counter 514 counts the number of sectors sent from the input control device 513 to the decryption device 512. When the number of sectors counted (called the counter value M hereunder) reaches a predetermined value (called the threshold Mmax hereunder), the sector transfer counter 514 instructs the input control device 513 not to input the sector data and gives the message forwarding device 516 an instruction to forward a message.

The threshold Nmax set for the sector transfer counter 523 in the host 502 is assumed to be smaller than the threshold Mmax set for the sector transfer counter 514 in the drive unit 514 (condition: Nmax<Mmax).

Although it is assumed here that when the counter value M reaches the threshold Mmax, the sector transfer counter 514 instructs the input control device 513 not to input the sector data, the input control device 513 may be instructed not to transfer the input sector data to the decryption device 512.

The reset processing device 515 is provided to reset the counter value M on the sector transfer counter 514 to zero. Instructions to the reset processing device 515 are given by the command processing device 517.

Figure 22:
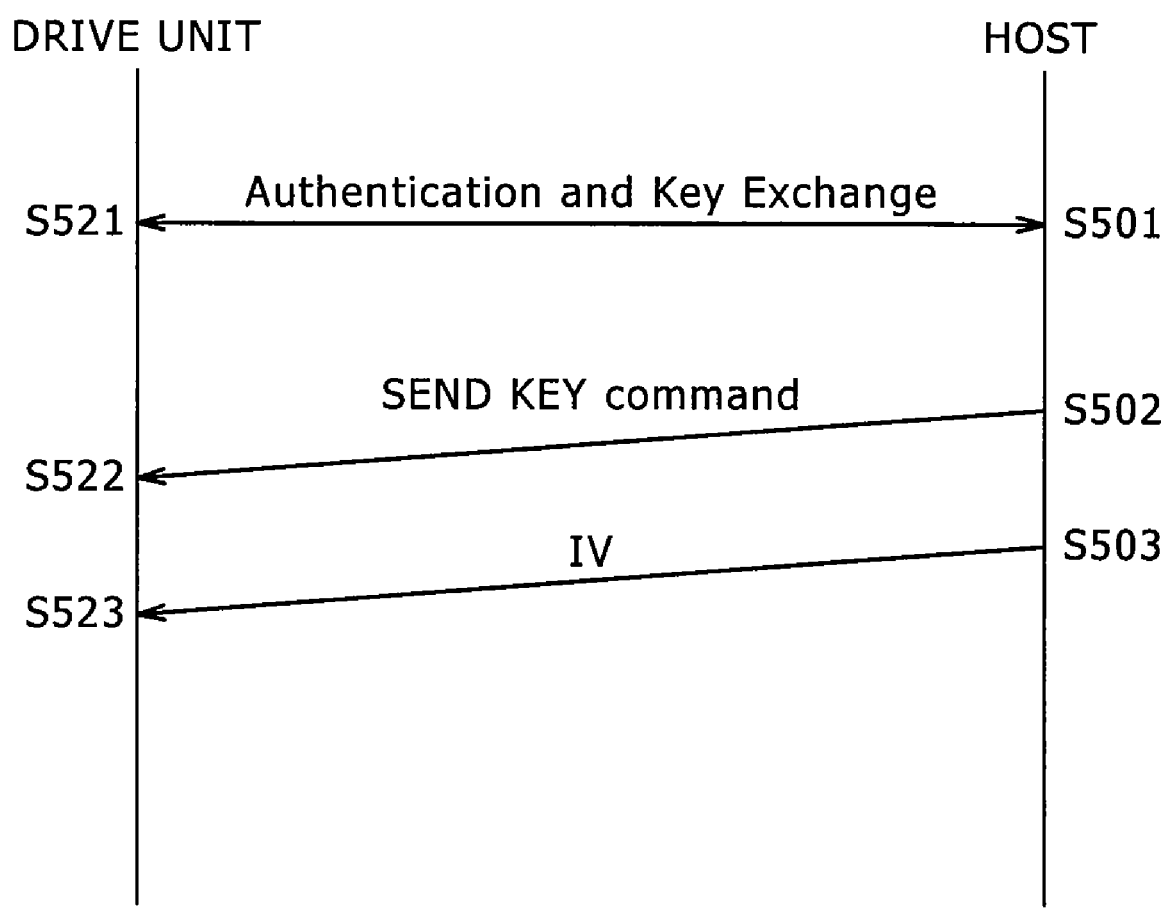
[FIG. 22]

How the system of the above-described structure operates will now be described. First to be explained in reference to the timing chart of FIG. 22 is the processing associated with the initializing vector IV. The host 502 and the drive unit 501 authenticate one another in steps S501 and S521, respectively. Control is passed on to the next step only after a successful completion of the mutual authentication. Following the mutual authentication, the authentication processing device 511 in the drive unit 501 and the authentication processing device 521 in the host 502 generate the session key Ks each (for shared use).

In step S502, the host 502 generates a SEND KEY command 563 and outputs it to the drive unit 501. The SEND KEY command 563 generated and output in step S502 is used to have the initializing vector IV transferred.

In step S503, the initializing vector IV is generated and transferred. Transfer of the initializing vector IV is executed by use of the SEND KEY command 563. The drive unit 501 receives the SEND KEY command 563 and the initializing vector IV in steps S522 and S523, respectively. The command processing device 517 forwards the received SEND KEY command 563 to the reset processing device 515.

Upon receipt of the SEND KEY command 563, the reset processing device 515 gives the sector transfer counter 514 an instruction to reset the counter value M (to zero). The initializing vector IV, included in the SEND KEY command 563, is sent to the decryption device 512.

Figure 23:
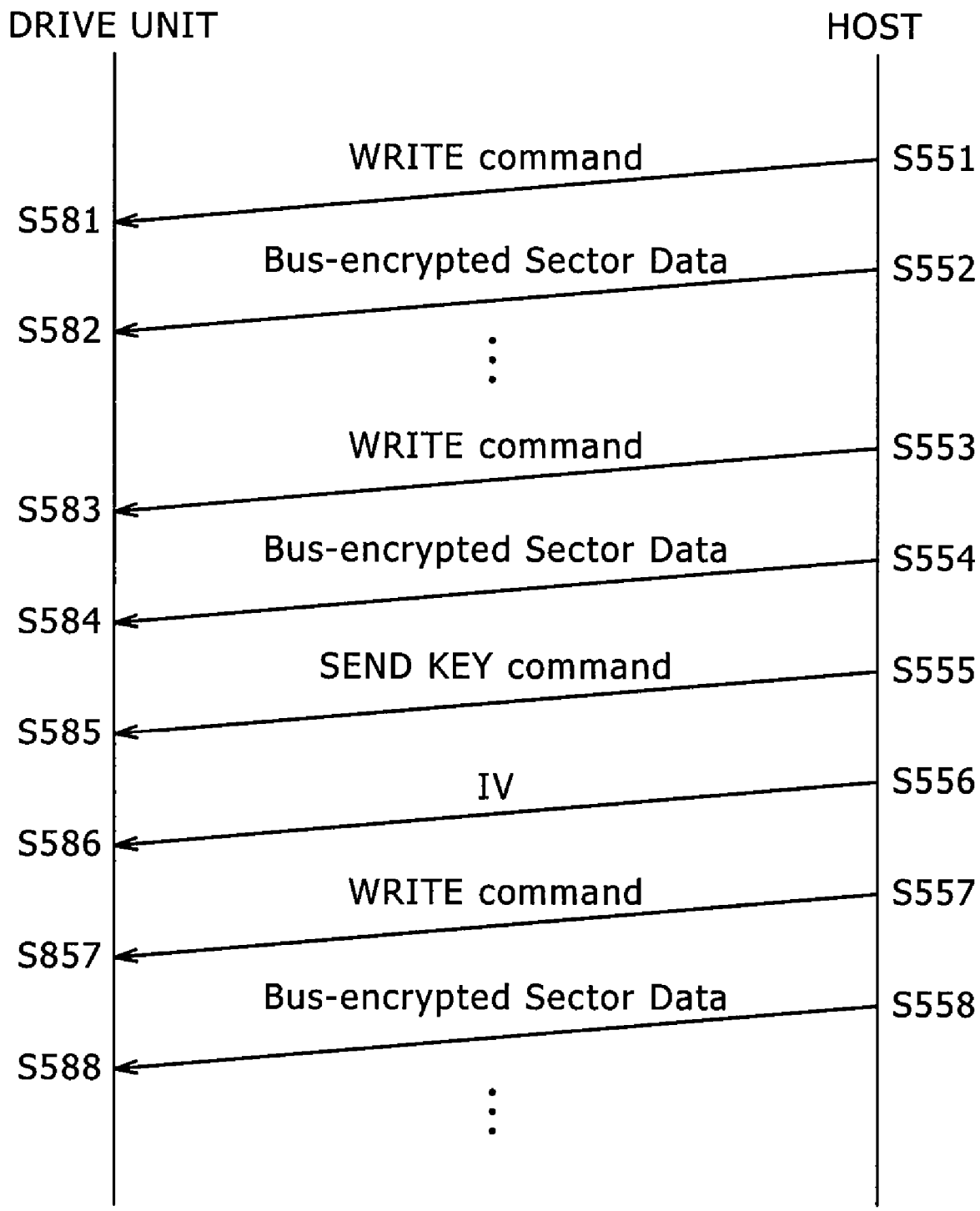
[FIG. 23]

As described above, the drive unit 501 and the host 502 share the session key Ks and the initializing vector IV. What takes place after the session key Ks and initializing vector IV are shared between the two sides is described below with reference to the timing chart of FIG. 23.

In step S551, the host 502 sends a WRITE command designating the writing of sector data. In step S552, the encryption device 522 of the host 502 encrypts the sector data 561 using the session key Ks and initializing vector IV, and sends the encrypted data (Bus-Encrypted Sector Data) to the drive unit 501. The input control device 513 in the drive unit 501 forwards the supplied Bus-Encrypted Sector Data to the decryption device 512.

The decryption device 512 decrypts the received data using the session key Ks from the authentication processing device 511 and the initializing vector IV generated and supplied by the random number generation device 524, thereby generating the sector data 551. The sector data 551 thus generated is written to the disc 503 under control of the access processing device 518.

During the processing above, the sector transfer counter 523 in the host 502 counts the number of sectors having been sent, and checks to determine whether the counter value N being counted has become larger than the value Nmax. As the counter value N becomes larger (i.e., as the sector data is transmitted consecutively), there comes a time when the counter value N becomes larger than the threshold Nmax (i.e., condition of N>Nmax is met).

When the counter value N is found to be larger than the threshold Nmax, the host 502 transmits the SEND KEY command 563. In the timing chart of FIG. 23, the SEND KEY command 563 is transmitted in step S555.

The SEND KEY command 563 sent from the host 502 is received by the drive unit 501 in step S585. With the SEND KEY command 563 received, the sector transfer counter 514 of the drive unit 501 is reset. As long as the SEND KEY command 563 is output in a suitably timed manner from the host 502, the counter value M on the sector transfer counter 514 will not exceed the threshold Mmax. This forestalls the state in which the input control device 513 rejects data input. Thus the sector data is allowed to be written continuously to the disc 503.

Figure 24:
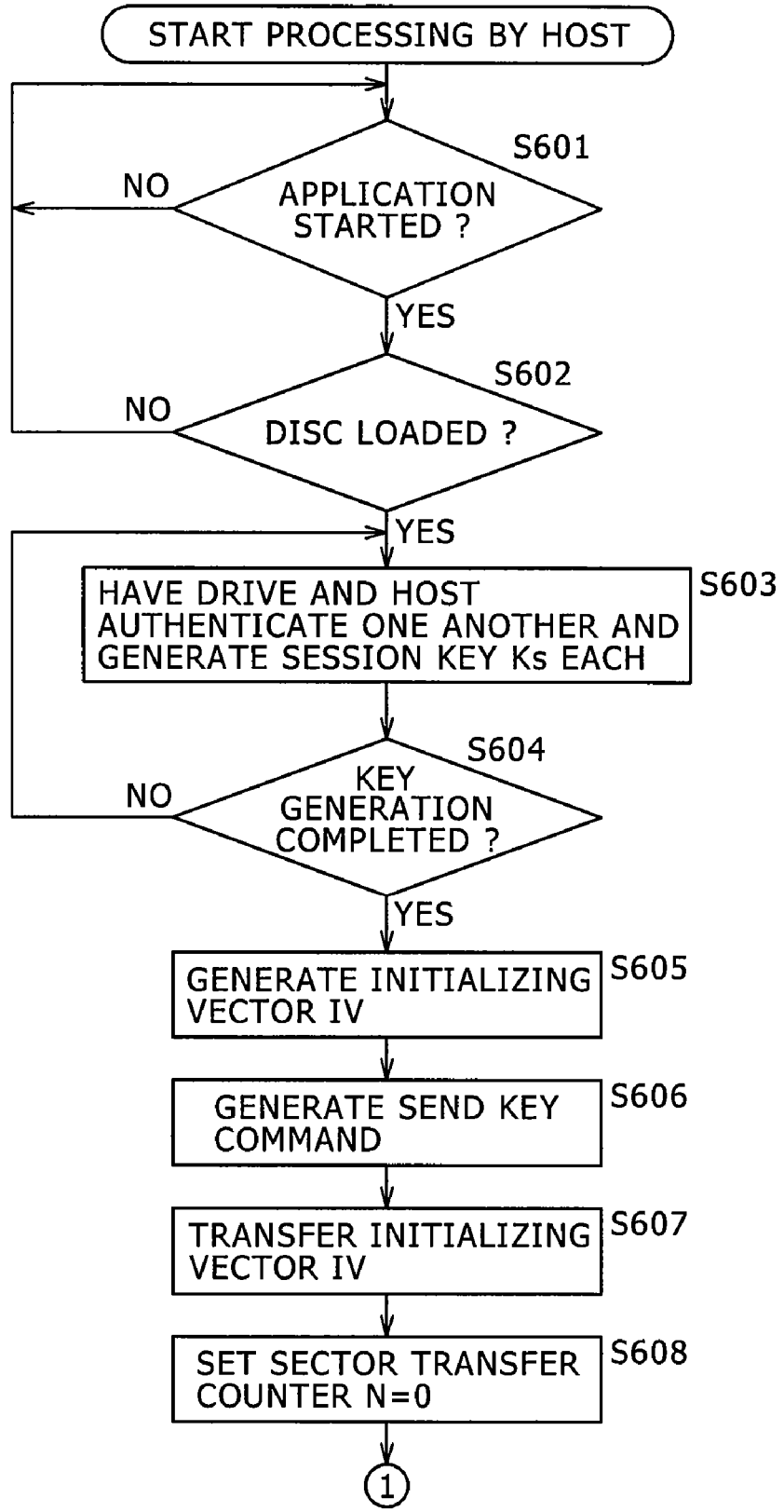
[FIG. 24]
Figure 25:
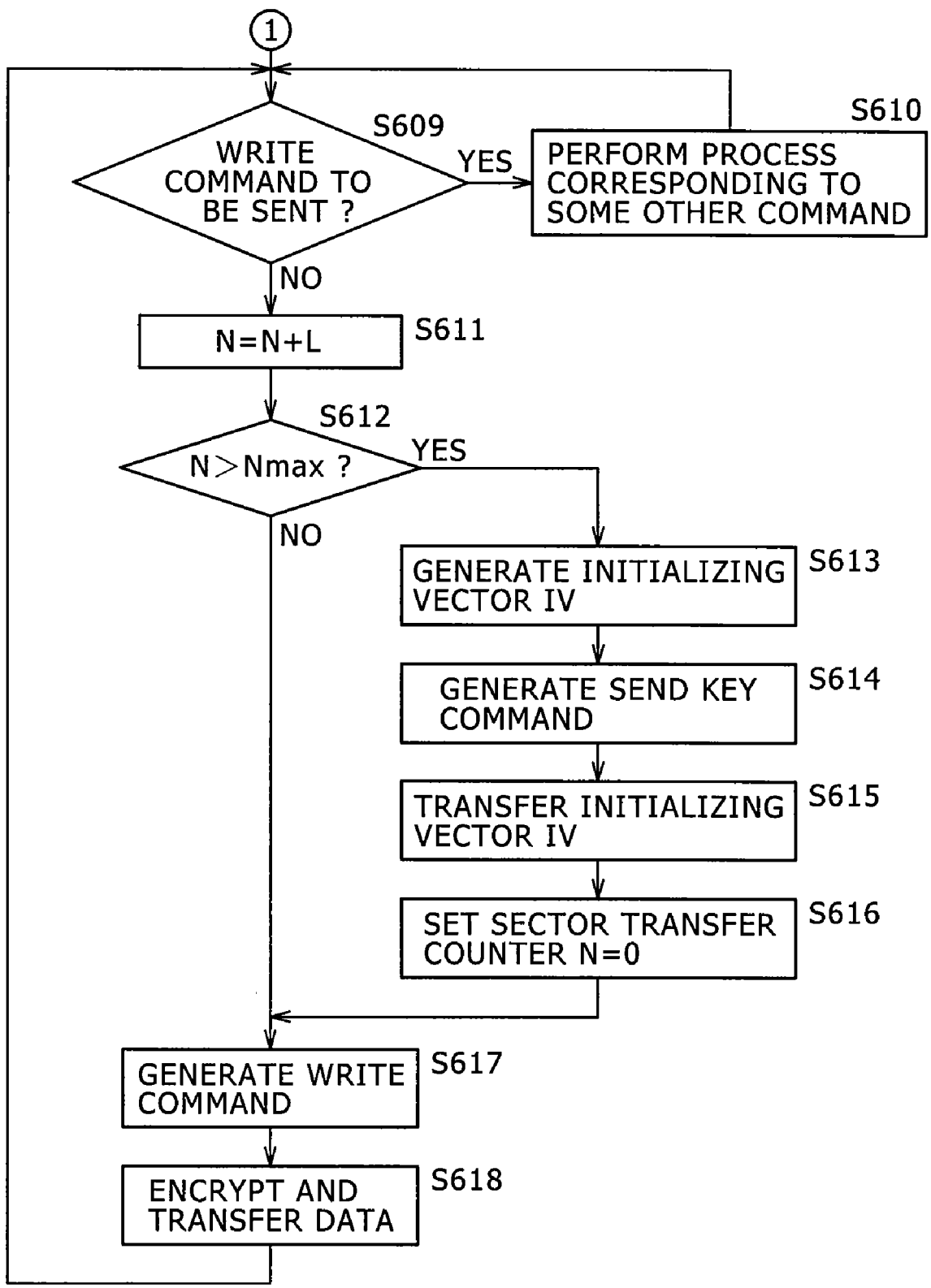
[FIG. 25]

How each of the drive unit 501 and the host 502 works will now be described. The processing performed by the host 502 is explained first by referring to the flowcharts of FIGS. 24 and 25. In step S601, the host 502 checks to determine whether an appropriate application is being started up. The appropriate application is an application necessary for writing data to the disc 503 loaded in the drive unit 501.

If in step S601 the application is found started up, step S602 is reached. In step S602, a check is made to determine whether the disc 503 is loaded in the drive unit 501. If in step S602 the disc 503 is found loaded in the drive unit 501, step S503 is reached in which the drive unit 501 and the host 502 authenticate one another. The drive unit 501 and the host 502 generate a session key Ks each (for shared use).

In step S604, a check is made to determine whether generation of the session key Ks is completed. Steps S603 and S604 are repeated until the generation of the session key Ks is found complete.

If in step S604 the generation of the session key Ks is found to be completed, step S605 is reached. In step S605, an initializing vector IV is generated. In step S606, the SEND KEY command 563 is generated. In step S607, the initializing vector IV is sent to the drive unit 501 by use of the generated SEND KEY command 563.

In step S608, the counter value N on the sector transfer counter 523 is set to zero. In step S609 (of FIG. 25), a check is made to determine whether a WRITE command is to be transmitted. If a command other than the WRITE command is found to be transmitted, step S610 is reached. In step S610, the process relevant to the other command is carried out.

If in step S609 the WRITE command is found to be transmitted, step S611 is reached. In step S611, the counter value N counted on the sector transfer counter 523 is updated to N+L. Reference character L stands for a value written in the Transfer Length field as part of the WRITE command. Since the Transfer Length is data which designates the number of sectors to be written as mentioned earlier, the value L corresponds to the number of sector data to be sent at that point.

In step S612, a check is made to determine whether the counter value N counted on the sector transfer counter 523 is larger than the threshold Nmax (i.e., whether the condition of N>Nmax is met). If in step S612 the condition of N>Nmax is found met, step S613 is reached. That the condition of N>Nmax is set signifies that now is the time to send the SEND KEY command 563 or transmit (i.e., to update) the initializing vector IV.

What takes place in steps S613 to S616 is the same as the process of steps S606 to S608. That is, the SEND KEY command 563 and initializing vector IV are generated anew and sent to the drive unit 501.

If in step S612 the condition of N>Nmax is not found met, step S617 is reached. In step S617, the WRITE command is generated and transmitted. In step S618, the sector data 561 is encrypted by the encryption device 522, and the encrypted sector data 561 is sent to the drive unit 501.

Figure 26:
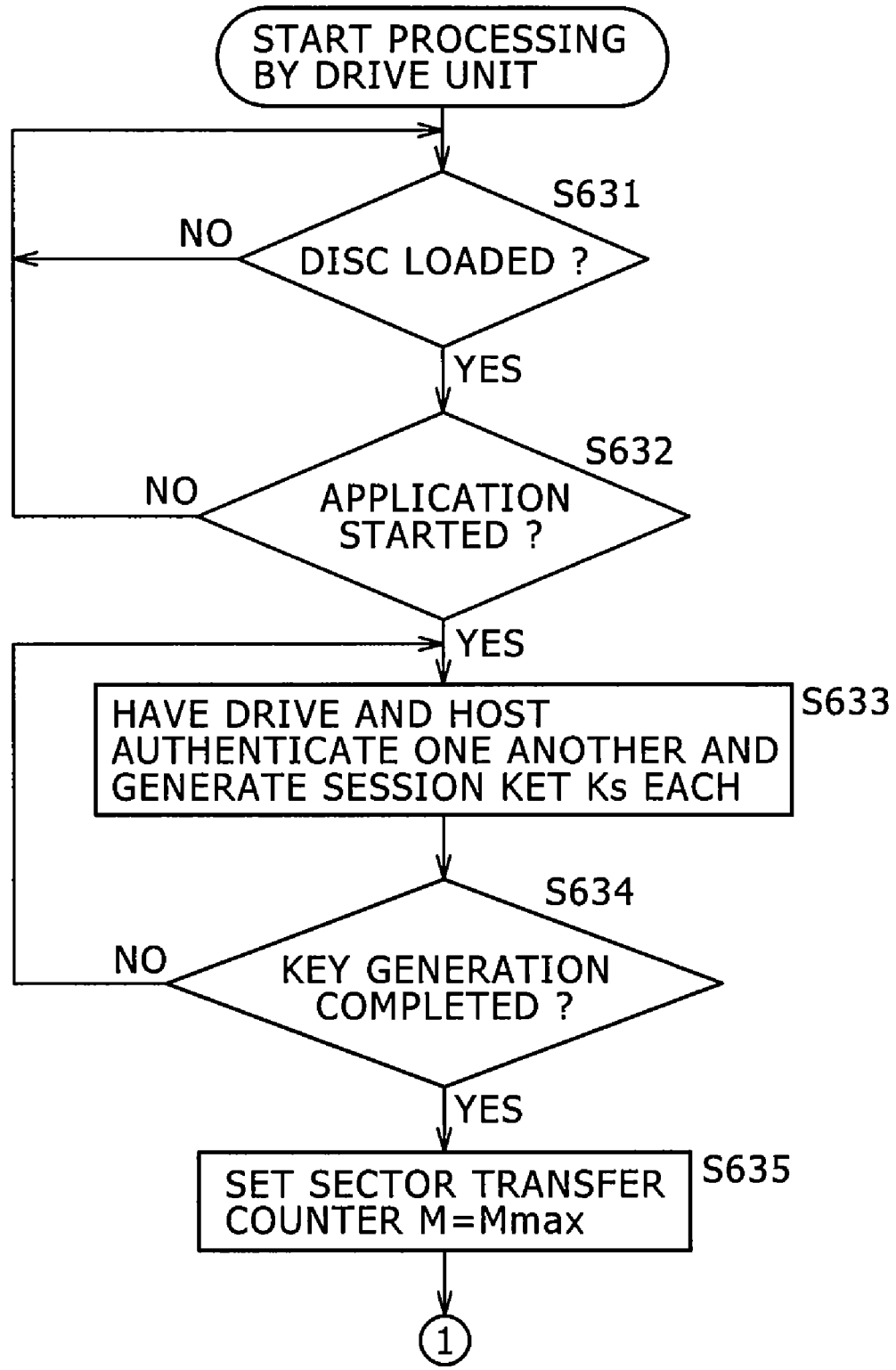
[FIG. 26]
Figure 27:
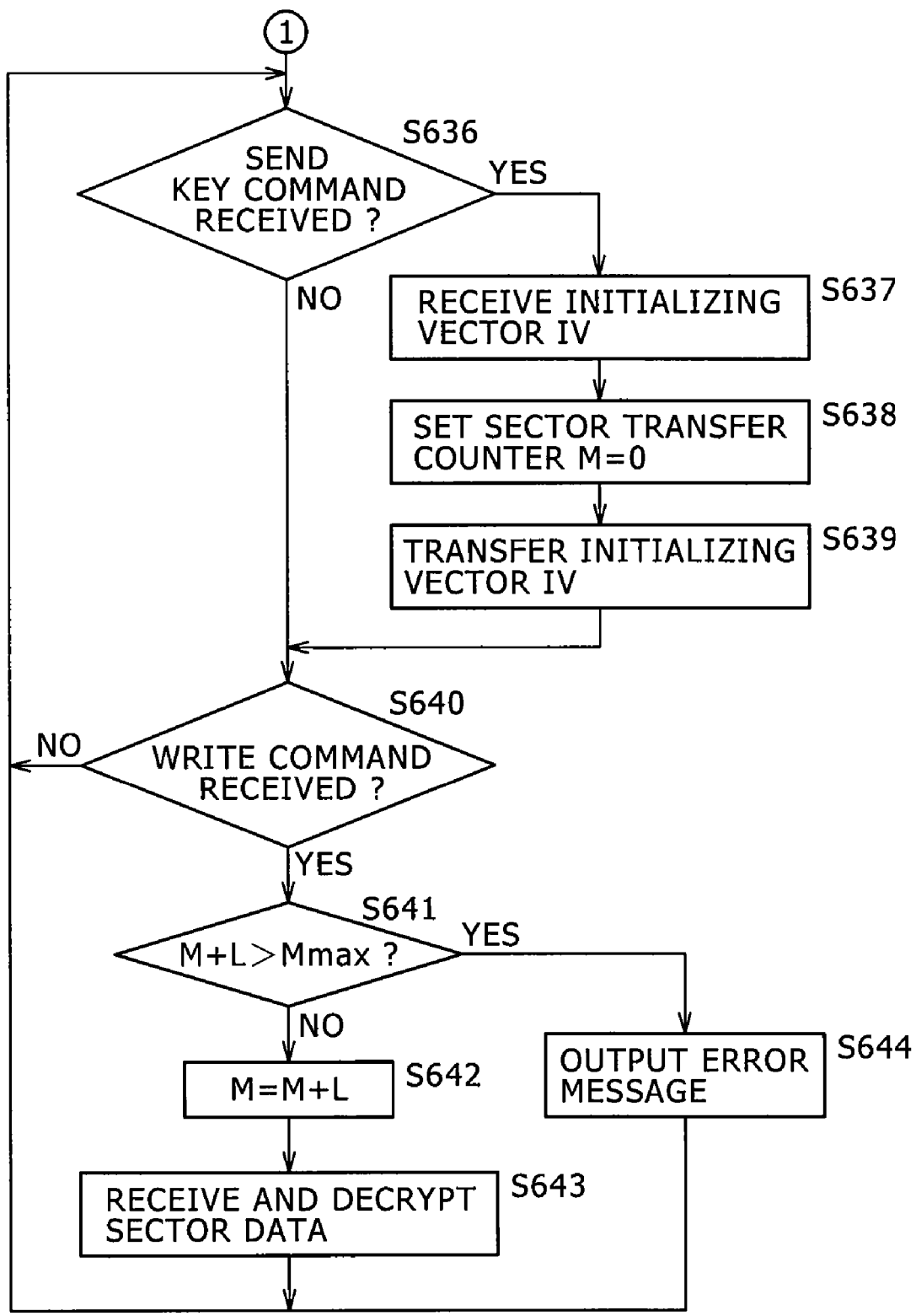
[FIG. 27]

While the processing above is being carried out by the host 502, the steps shown in the flowcharts of FIGS. 26 and 27 are performed by the drive unit 501.

In step S631, the drive unit 501 checks to determine whether the disc 503 is loaded. If in step S631 the disc 503 is found loaded in the drive unit 501, step S632 is reached. In step S632, a check is made to determine whether the suitable application is being started up by the host 502.

If in step S632 the application in question is found started up, step S633 is reached. In step S633, the drive unit 501 and the host 502 authenticate one another. The drive unit 501 and host 502 generate the session key Ks each (for shared use).

In step S634, a check is made to determine whether generation of the session key Ks is completed. Steps S633 and S634 are repeated until the generation of the session key Ks is found complete. When the generation of the session key Ks is found to be completed in step S634, step S635 is reached.

In step S635, the counter value M on the sector transfer counter 514 is set to the threshold Mmax. With M=Mmax established, the sector transfer counter 514 issues an instruction preventing the input control device 513 from inputting data from the host 502.

In step S636 (of FIG. 27), a check is made to determine whether the SEND KEY command 563 is received. If the SEND KEY command 563 is found received, step S637 is reached. In step S637, the initializing vector IV that was sent in response to the SEND KEY command 563 is received. With the SEND KEY command received, the reset processing device 515 gives the sector transfer counter 514 an instruction to reset the counter value M to zero.

Given the instruction, the sector transfer counter 514 resets the counter value M to zero in step S638. When the counter value M on the sector transfer counter 514 is reset to zero (i.e., when the counter value is made smaller than the threshold Mmax), the input of data to the input control device 613 is authorized.

In step S639, the initializing vector IV is supplied to the decryption device 512. In step S640, a check is made to determine whether the WRITE command 564 is received. If in step S640 the WRITE command 564 is not found received, step S636 is reached again and the subsequent steps are repeated. If in step S640 the WRITE command 564 is found received, step S641 is reached.

In step S641, a check is made to determine whether the counter value M on the sector transfer counter 514, supplemented by the value L of the Transfer Length (i.e., M+L) is larger than the threshold Mmax (i.e., whether the condition of M+L>Mmax is met). If in step S641 the condition of M+L>Mmax is not found met, step S642 is reached. In step S642, the counter value M is updated to M+L. That the condition of M+L>Mmax is not met signifies the state in which the input of data to the input control device 513 is authorized.

In step S643, the encrypted sector data 561 is received. The received sector data 561 is decrypted by the decryption device 512 and written to the disc 503 as the sector data 551.

If in step S641 the condition of M+L>Mmax is found met, step S644 is reached. Where the condition of M+L>Mmax is met, the counter transfer counter 514 gives the input control device 513 an instruction to stop inputting sector data and instructs the message forwarding device 516 to transmit a message.

The message to be sent from the message forwarding device 516 is an error message bringing the host 502 to recognize that the input of sector data is not authorized (i.e., the writing of sector data to the disc 503 is not allowed). With the error message transmitted in step S644, step S636 is reached again and the subsequent steps are repeated.

When the error message is output, the host 502 recognizes the state the drive unit 501 is in, and proceeds to issue the SEND KEY command and supply the initializing vector IV. When the SEND KEY command is found received in step S636, step S637 is reached and the subsequent steps are carried out. This again brings about the state in which the input of sector data is authorized.

When the initializing vector IV is generated by the host 502 and the valid period (service life) of the vector IV is managed thereby as described, security is enhanced in the sending and receiving of data between the drive unit and the host.

The second embodiment described above thus offers the same benefits as those provided by the first embodiment explained earlier.

The series of steps and processes described above may be executed either by hardware or by software. For the software-based processing to take place, the programs constituting the software may be either incorporated beforehand in dedicated hardware of a computer or installed upon use from a suitable recording medium into a general-purpose personal computer or like equipment capable of executing diverse functions based on the installed programs.

The recording medium is offered to users not only as a package medium apart from their computers that handle the medium and constituted by a magnetic disc (including flexible discs), an optical disc (including CD-ROM (Compact Disc-Read Only Memory) and DVD (Digital Versatile Disc)), a magneto-optical disc (including MD (Mini-disc: registered trademark)), or a semiconductor memory, each medium carrying the necessary programs; but also in the form of a ROM or a hard disc drive, each accommodating the programs and incorporated beforehand in the user's computer.

In this description, the steps which describe the programs offered on the recording medium represent not only the processes that are to be carried out in the depicted sequence (i.e., on a time series basis) but also processes that may be performed parallelly or individually and not chronologically.

In this description, the term "system" refers to an entire configuration made up of a plurality of component devices or apparatuses.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. An information processing apparatus comprising:
   at least one processor;
   at least one memory device storing instructions, which when executed by the at least one processor, cause the at least one processor to:
   (a) cause a transfer controller to control transfer of data;
   (b) count a number of times said transfer controller has controlled the transfer of said data;

(c) determine whether the number is at least equal to a predetermined maximum count;
(d) if said number of times is at least equal to said predetermined maximum count, give an instruction to stop the transfer of said data;
(e) generate an initializing vector for use in either encrypting or decrypting said data;
(f) determine whether an instruction to have said initializing vector supplied is given by an external apparatus;
(g) if the instruction to have said initializing vector supplied is given by said external apparatus:
   (i) generate said initializing vector;
   (ii) reset the number of times having been counted; and
   (iii) transfer said initializing vector to said external apparatus;
(h) if the instruction to stop the transfer of said data is given, output to said external apparatus a message indicating that the transfer of said data is stopped;
(i) after said instruction to generate the initializing vector is given, determine whether said external apparatus requests a reissue of said initializing vector; and
(j) if the external apparatus requests the reissue of said initializing vector:
   (i) generate a reissue initializing vector;
   (ii) reset the number of times having been counted; and
   (ii) transfer said reissue initialing vector to said external apparatus.

2. An information processing method comprising:
causing a transfer controller to control transfer of data;
counting a number of times said transfer controller has controlled the transfer of said data;
determining whether the number of times counted is at least equal to a predetermined maximum count;
if said number of times is at least equal to said predetermined maximum count, giving an instruction to stop the transfer of said data;
generating an initializing vector for use in either encrypting or decrypting said data;
determining whether an instruction to have said initializing vector supplied is given by an external apparatus;
if the instruction to have said initializing vector supplied is given by said external apparatus:
   (a) generating said initializing vector;
   (b) resetting the number of times having been counted; and
   (c) transferring said initializing vector to said external apparatus;
if the instruction to stop the transfer of said data is given, outputting to said external apparatus a message indicating that the transfer of said data is stopped;
after said instruction to generate the initializing vector is given, determining whether said external apparatus requests a reissue of said initializing vector; and
if the external apparatus requests the reissue of said initializing vector:
   (a) generating a reissued initializing vector;
   (b) resetting the number of times having been counted; and
   (c) transferring said reissued initializing vector to said external apparatus.

3. A computer readable medium encoded with a program for causing a computer to carry out a procedure comprising the steps of;
causing a transfer controller to control transfer of data;
counting a number of times said transfer controller has controlled the transfer of said data;
determining whether the number of times counted is at least equal to a predetermined maximum count;
if said number of times is at least equal to said predetermined maximum count, giving in an instruction to stop the transfer of said data;
generating an initializing vector for use in either encrypting or decrypting said data;
determining whether an instruction to have said initializing vector supplied is given by an external apparatus;
if the instruction to have said initializing vector supplied is given by said external apparatus:
   (a) generating said initializing vector;
   (b) resetting the number of times having been counted; and
   (c) transferring said initializing vector to said external apparatus;
if the instruction to stop the transfer of said data is given, outputting to said external apparatus a message indicating that the transfer of said data is stopped;
after said instruction to generate the initializing vector is given, determining whether said external apparatus requests a reissue of said initializing vector; and
if the external apparatus requests the reissue of said initializing vector:
   (a) generating a reissued initializing vector;
   (b) resetting the number of times having been counted; and
   (c) transferring said reissued initialing vector to said external apparatus.

4. A recording medium which records a computer-readable program for causing a computer to carry out a procedure comprising the steps of;
causing a transfer controller to control transfer of data;
counting a number of times said transfer controller has controlled the transfer of said data;
determining whether the number of times counted is at least equal to a predetermined maximum count;
if said number of times is at least equal to said predetermined maximum count, giving an instruction to stop the transfer of said data;
generating an initializing vector for use in either encrypting or decrypting said data;
determining whether an instruction to have said initializing vector supplied is given by an external apparatus;
if the instruction to have said initializing vector supplied is given by said external apparatus:
   (a) generating said initializing vector;
   (b) resetting the number of times having been counted; and
   (c) transferring said initializing vector to said external apparatus
if the instruction to stop the transfer of said data is given, outputting to said external apparatus a message indicating that the transfer of said data is stopped;
after said instruction to generate the initializing vector is given, determining whether said external apparatus requests a reissue of said initializing vector; and
if the external apparatus requests the reissue of said initializing vector:
   (a) generating a reissued initializing vector;
   (b) resetting the number of times having been counted; and
   (c) transferring said reissued initialing vector to said external apparatus.

* * * * *